United States Patent [19]
Yoshimoto et al.

[11] Patent Number: 5,399,703
[45] Date of Patent: Mar. 21, 1995

[54] TETRAZOLE DERIVATIVES AND DRUGS

[75] Inventors: Yoshihiko Yoshimoto; Shoji Yasufuku, both of Shiga; Yoshihiko Makita, Osaka; Kichiro Inoue; Kei Nakanouchi, both of Kyoto, all of Japan

[73] Assignee: Nippon Shinyaku Company, Limited, Japan

[21] Appl. No.: 966,022

[22] PCT Filed: Jun. 20, 1991

[86] PCT No.: PCT/JP91/00830
§ 371 Date: Feb. 4, 1993
§ 102(e) Date: Feb. 4, 1993

[87] PCT Pub. No.: WO92/00285
PCT Pub. Date: Jan. 9, 1992

[30] Foreign Application Priority Data

Jun. 22, 1990 [JP] Japan .................. 2-165067
Jan. 31, 1991 [JP] Japan .................. 3-032327
Mar. 27, 1991 [JP] Japan .................. 3-089623

[51] Int. Cl.⁶ .................. C07D 257/04; C07D 403/12; A61K 31/41; A61K 31/47
[52] U.S. Cl. .................. 548/253; 546/175

[58] Field of Search .................. 548/253; 514/381, 314; 546/175

[56] References Cited
U.S. PATENT DOCUMENTS 4,372,953  2/1983  Uchida et al. .................. 424/248.5
4,661,505  4/1987  Marshall et al. .................. 514/381

*Primary Examiner*—David B. Springer
*Attorney, Agent, or Firm*—Rosenman & Colin

[57] ABSTRACT

A compound of the formula [I] useful for treating allergic symptoms, cardiovascular disorders, cerebrovascular disorders, inflammation or other conditions mediated by SRS-A in humans and animals is disclosed.

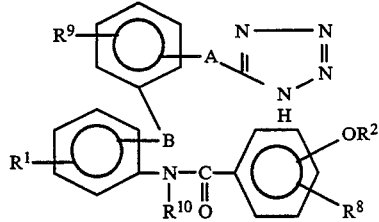

31 Claims, No Drawings

TETRAZOLE DERIVATIVES AND DRUGS

The present invention relates to a tetrazole derivative of the following general formula [I] or a pharmacologically acceptable salt thereof.

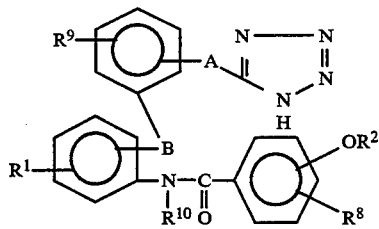

[I]

wherein A means $-(O)m-(CH(R^4))n-$ ($R^4$ is hydrogen or alkyl; m and n each is 0 or 1); B means oxygen or $-S(O)p-$ (p is 0 to 2) ; $R^1$ means hydrogen, lower alkyl, lower alkoxy, halogen, haloalkyl or hydroxy; $R^2$ means alkyl, alkenyl or aralkyl, which may be substituted or unsubstituted; $R^8$ means hydrogen, lower alkoxy or halogen; $R^9$ means hydrogen, lower alkyl, lower alkoxy, lower acyloxy, halogen, nitro or hydroxy; $R^{10}$ means hydrogen or lower alkyl.

The compound according to the invention has antiallergy and antiinflammatory activities and is of use for alleviation and relief of allergic symptoms such as bronchial asthma, urticaria, allergic rhinitis and atopic dermatitis or as a therapeutic agent for cardiovascular disorder, cerebrovascular disorder, inflammation, arthritis and other diseases.

BACKGROUND ART

It is generally believed that allergic asthma and atopic diseases are induced as a variety of chemical mediators are released from the lung and other tissues to contract smooth muscles such as the bronchial muscle and pulmonary blood vessels or increase the permeability of blood vessels of the skin to thereby inflict various damages on various tissues.

Of such chemical mediators, histamine and SRS-A have been considered to be of the greatest significance. Recently, SRS-A was identified to be a mixture of leukotrienes $LTC_4$, $LTD_4$ and $LTE_4$, which are peptides, and the multi-pronged physiological action of these leukotrienes (LT) and their association with various pathologic states have been extensively explored. By origin, SRS-A is a lipoxygenase-catalyzed metabolite of arachidonic acid and much interest has been focused on the role it plays as a substance involved in the onset or progression to refractoriness of bronchial asthma and other diseases arising from immediate type allergic reactions.

In fact, $LTC_4$ and $LTD_4$ strongly contract the isolated guinea pig and human tracheas and enhance the secretion of mucus from the human respiratory tract in vitro. Therefore, particular attention has been paid to their involvement in bronchial asthma.

Clinically, too, LT has been demonstrated in the sputum of patients with, for example, bronchitis in concentrations sufficient to produce physiological changes. It has also been reported that, in children with bronchial asthma, the blood $LTC_4$ level is well correlated with the severity of the disease.

Asthma being set aside, it has been suggested that LT is associated with allergic rhinitis and dermatitis and even with ischemic diseases such as myocardial infraction etc., cardiac anaphylaxis, endotoxin shock, psoriasis and so forth.

Therefore, there is a mounting interest in the development of drugs which would either inhibit the production of SRS-A or antagonize SRS-A.

Thus, for example, FPL-55712, SKF-104353, WY-45911 and ONO-1078, among others, are known as LT antagonists. However, none have been commercially available as yet. [Tohn H. Müsser et al., New development concerning Leukotriene Antagonists. Agents and Actions, 18 (¾) 332 (1986), Drugs of the Future, 13(4) 317 (1988)].

Japanese Kokai Tokkyo Koho 62-198652 describes a group of compounds not alien to the compound of this invention, with the comment that some of the compounds have 5α-reductase inhibitory activity. The description in the claim of the corresponding specification might suggest that the compound of the present invention is subsumed therein but nowhere in the same specification is found a specific disclosure of any compound having a tetrazoyl group. Furthermore, there is no statement suggestive of the pharmacologic actions characteristic of the compound of the present invention. Incidentally, it has been proven that the compound of the present invention has no 5α-reductase activity at all.

DISCLOSURE OF INVENTION

The inventors of the present invention have done much research to obtain a compound which would have the property to inhibit the production of SRS-A or antagonize SRS-A and be superior to the hitherto-known antiallergic and antiinflammatory drugs in efficacy, safety and duration of action. Thus, the object of the invention is the provision of a novel compound having improved antiallergy and antiinflammatory activities.

The essence of the present invention lies in the very structure of the compound represented by general formula [I].

The compound provided by the present invention is not only a novel compound not heretofore described in the literature but also a compound which has excellent pharmacological activities, good bioavailability, long duration of action and low toxicity as will be described hereinafter and is, therefore, of value as a medicament.

The compound of the present invention, which may be represented by general formula [I], is now described in detail.

Referring to $R^1$ in general formula [I], the halogen may be chlorine, fluorine, bromine or iodine.

The lower alkyl is preferably a straight-chain or branched group of 1 to 4 carbon atoms, such as methyl, ethyl, n-propyl, isopropyl, n-butyl, isobutyl, sec-butyl and so on.

The lower alkoxy is preferably a straight-chain or branched group of 1 to 4 carbon atoms, such as methoxy, ethoxy, n-propoxy, isopropoxy, n-butoxy, isobutoxy, sec-butoxy and so on.

The haloalkyl is preferably a straight-chain or branched alkyl group of 1 to 4 carbon atoms substituted by one or more fluorine, chlorine, bromine or iodine atoms, such as trifluoromethyl, trichloromethyl, difluoromethyl, 2-trifluoroethyl, 3-trifluoropropyl, 4-trifluorobutyl and so on.

Referring to $R^2$, the alkyl is preferably a group of 1 to 10 carbon atoms. As such, there may be mentioned, in addition to the alkyl groups mentioned above, such other groups as pentyl, isopentyl, hexyl, isohexyl, heptyl, isoheptyl and so on.

The alkenyl is preferably a straight-chain or branched group of 2 to 10 carbon atoms, such as vinyl, allyl, isopropenyl, 2-methallyl, 2-butenyl, 3-butenyl, pentenyl, isopentenyl, hexenyl, isohexenyl, heptenyl, isoheptenyl and so on.

The aralkyl is preferably a group of 7 to 12 carbon atoms, such as benzyl, phenethyl, phenylpropyl, phenylbutyl, phenylpentyl, phenylhexyl, naphthylmethyl and so on.

Among substituents for said alkyl are —COOR$^3$ (R$^3$ is hydrogen or C$_{1-6}$ alkyl which may be unsubstituted or substituted by —CON(R$^6$)R$^7$ (R$^6$ and R$^7$ may be the same or different and each is hydrogen or lower alkyl), hydroxy, —CON(R$^6$)R$^7$ (R$^6$ and R$^7$ may be the same or different and each is hydrogen or lower alkyl) or a heterocyclic group. The heterocyclic group includes, among others, unsubstituted or halogen-substituted quinoline, tetrazole and other groups.

Referring to R$^4$, the alkyl group includes those species of alkyl mentioned above by way of example for R$^1$.

The lower alkoxy for R$^8$ includes those species of alkoxy mentioned above by way of example for R$^1$. The halogen includes those species of halogen mentioned by way of example for R$^1$.

The lower alkyl, lower alkoxy and halogen for R$^9$ include those species of alkyl, alkoxy and halogen mentioned above by way of example for R$^1$.

The lower acyloxy is preferably a straight-chain or branched group of 2 to 5 carbon atoms, such as acetoxy, propionyloxy, butyryloxy, isobutyryloxy, valeryloxy, isovaleryloxy and so on.

The lower alkyl for R$^{10}$ includes those species of lower alkyl mentioned above by way of example for R$^1$.

The salt includes, among others, not only alkali metal or alkaline earth metal salts, such as sodium salt, calcium salt, etc. but also organic amine salts, amino acid salts and ammonium Salts.

The compound of this invention can be produced by the following and other processes.

Process A

Process B

In the above formulas, A, B, R$^1$, R$^2$, R$^8$, R$^9$ and R$^{10}$ are as defined hereinbefore.

Process A

An aniline derivative [II] is reacted with a benzoic acid derivative [III] or a reactive derivative of [III] to provide [I].

This acylation reaction can be carried out by the per se known methods.

For example, there can be employed the method employing a reactive derivative of [III], such as a benzoyl halide derivative (e.z. benzoyl chloride derivative, benzoyl bromide derivative, etc.), a lower alkyl ester or active ester (e.g. p-nitrophenyl ester, p-nitrobenzyl ester, p-chlorophenyl ester, etc.), an imidazolide or mixed acid anhydride (e.g. mixed anhydrides with lower alkyl carbonates or lower alkylphosphates), or the method involving a direct condensation between [II] and [III] with the aid of a condensing agent.

When a benzoyl halide derivative is employed, usually this benzoyl halide derivative is reacted with [II] in the presence of an organic base, or in the absence thereof, in an inert solvent at a temperature of −5° C. to 120° C. The solvent inert to the reaction includes, among others, ethers such as diethyl ether, tetrahydrofuran, dioxane, etc., halogenated hydrocarbons such as methylene chloride, chloro-form, etc., hydrocarbons such as benzene, toluene, xylene, etc., aprotic solvents such as N,N-dimethylformamide etc., and various mixtures of such solvents.

The organic base includes, among others, tertiary organic bases such as pyridine, triethylamine, tributylamine, dimethylaniline and so on.

The reaction time varies with the species of starting materials, base and solvent used but generally may range from about 30 minutes to about 12 hours.

The preferred proportions of said benzoyl halide derivative and base are generally 1 to 3 moles per mole of [II].

When a direct condensation reaction is carried out with the aid of a condensing agent, [II] is reacted with [III] in the presence of the condensing agent generally in a solvent inert to the reaction at −20° to 80° C. As the solvent, those mentioned hereinbefore can be employed.

The condensing agent that can be used includes, among others, carbodiimides such as dicyclohexylcarbodiimide etc., quaternary pyridinium salts such as 2-chloro-N-methylpyridinium iodide, 2-methanesulfonyloxy-N-methylpyridinium iodide, etc., diphenyl phosphoryl azide, diethyl phosphoryl cyanide, or triphenylphosphine and carbon tetrachloride.

The reaction time, which varies with the species of starting materials, condensing agent and solvent used, may generally be about 30 minutes to 12 hours.

The preferred proportions of [III] and condensing agent are generally about 1 to 3 moles per mole of [II].

Process B

A cyano group-containing compound [IV] is reacted with hydrazoic acid or a salt thereof to give [I].

Among the salts of hydrazoic acid which can be used are salts of hydrazoic acid with alkali metals, such as sodium azide, potassium azide, lithium azide, etc., salts with alkaline earth metals such as calcium azide, magnesium azide, etc., salts with other metals capable of forming salts with hydrazoic acid, such as aluminum azide, tin azide, etc., or salts with organic bases such as tetramethylguanidinium azide and so on.

In the present invention, such salts of hydrazoic acid can be used independently. However, as an alternative, [I] can be produced by conducting the reaction in an inert solvent in the presence of such an alkali metal salt of hydrazoic acid (e.g. sodium azide) and a Lewis acid (e.g. aluminum chloride, tin(IV) chloride, zinc chloride, titanium chloride, $BF_3$-diethyl ether, etc.), an ammonium salt (e.g. ammonium chloride, di-n-butylammonium chloride, benzeneammonium chloride, tetramethylammonium chloride, etc.), a sulfonic acid (e.g. ethanesulfonic acid etc.), an alkali metal halide (e.g. lithium chloride) or an amine salt (e.g. triethylamine hydrochloride, pyridine hydrochloride, etc.) at a temperature between 0° C. and 200° C. The solvent that can be used includes, among others, aprotic solvents such as N,N-dimethylformamide, dimethyl sulfoxide, N-methylpyrrolidone, etc., ethers such as tetrahydrofuran, dioxane, methylcellosolve, ethylcellosolve, etc. and hydrocarbons such as benzene, toluene, petroleum ether and so on.

The proportion of the azide compound is 1 to 10 moles per mole of compound [IV]. The reaction time, which varies with the species of starting compound, salt and solvent used, may generally range from 30 minutes to 48 hours.

When the compound thus obtained is an ester ($R^3$=alkyl), it can be hydrolyzed to the object compound wherein $R^3$ is hydrogen. This hydrolysis reaction can be easily conducted in an appropriate solvent (e.g. alcohols such as methanol, ethanol, etc., glycols such as ethylene glycol, 2-methoxyethanol, etc., ethers such as tetrahydrofuran, 1,2-dimethoxyethane, etc., ketones such as acetone, methyl ethyl ketone, etc., water, or mixtures of them) in the presence of an alkali at a temperature of 0° to 100° C. for 30 minutes to 5 hours.

The alkali which can be used includes hydroxides such as sodium hydroxide, potassium hydroxide, lithium hydroxide, etc. and carbonates such as sodium carbonate, potassium carbonate and so on. The proportion of said alkali is generally 2 to 6 moles and preferably 3 to 4 moles per mole of the ester.

The carboxylic acid ($R^3$=H) thus obtained can be converted, if necessary, to an ester ($R^3$=alkyl). This esterification reaction can be carried out by the per se known esterification procedures, for example by using diazomethane, an alcohol and an acid (e.g. hydrogen chloride, sulfuric acid, p-toluenesulfonic acid, etc.), or thionyl chloride and an alcohol.

The compound [I] obtained as above can be reacted with a pharmaceutically acceptable organic amine, an alkali metal hydroxide or ammonia in the per se known manner, for example by admixing and heating them to give the corresponding organic amine salt, amino acid salt, alkali metal salt or ammonium salt of compound [I].

In the case of an alkali metal salt, for instance, the compound produced in the above manner can be reacted with, for example, sodium hydroxide in an alcohol or an aqueous alcohol under heating to obtain the salt.

The oxidation of the sulfur atom can be performed in the per se known manner.

Thus, this reaction is conducted using an oxidizing agent such as perbenzoic acid, ozone, phenyldichloroiodide, hydrogen peroxide, sodium metaperiodate, sodium hypochlorite and so on. Particularly preferred is m-chloroperbenzoic acid. Generally speaking, the sulfoxide (p=1) is obtained when the amount of the oxidizing agent is one equivalent with respect to compound [I] (p=0), while the sulfone (p=2) is obtained when 2 or more equivalents of the oxidizing agent is employed.

This reaction is generally conduced in an inert solvent, such as methylene chloride, chloroform, carbon tetrachloride, etc., at a temperature of −30° to 60° C. and the reaction time is about 3 minutes to 3 hours for the sulfoxide and about 1 to 48 hours for the sulfone.

While some species of the compound of the present invention contain asymmetric carbon, the respective optical isomers and racemic mixtures thereof all fall within the scope of the present invention. Separation of optical isomers from a racemic mixture obtained as above can be made by utilizing their acidity, for example by optical resolution with an optically active base (brucine, quinine, α-methylbenzylamine or the like) in the conventional manner. Such optical isomers can also be produced starting with the optically active compounds [II] through [IV].

The object compound [I] thus produced can be isolated and purified by per se known procedures such as concentration, pH adjustment, redistribution, solvent extraction, crystallization, fractional distillation, chromatography and so on.

The starting compounds [II] and [IV] can be produced by the processes described in Reference Examples given hereinafter.

For administration of the compound of the present invention as a drug to man or other animals, it can be administered as it is or as formulated beforehand into a pharmaceutical composition containing 0.01 to 99.5%, preferably 0.5 to 90%, of the compound in a pharmaceutically acceptable, nontoxic and inert excipient.

The excipient mentioned above may be one or more solid, semisolid or liquid diluents, fillers and/or other formulation auxiliaries. Such a pharmaceutical composition is preferably administered in unit dosage forms. The pharmaceutical composition of the invention can be administered intravenously, orally, into tissues, topically (instillation into the nose or the eye) or rectally. Of course, dosage forms suitable for the respective routes of administration should be employed. Particularly preferred are oral administration or inhalation.

The dosage as an antiallergic drug or an antiinflammatory drug should preferably be selected according to the patient's age, body weight and other characteristics, the route of administration and the nature and severity of the disease. The generally recommended dosage for oral administration to an adult human is 1 to 1000 mg/body/day or preferably 1 to 100 mg/body/day and that for inhalation is 0.01 to 100 mg/body/day. The required dosage may be somewhat less or more, depending on individual cases. The pharmaceutical composition may also be administered in 2 or 3 divided doses.

For oral administration, either solid or liquid unit dosage forms, such as neat powders, powders, tablets, dragees, capsules, granules, suspensions, solutions, syrups, drops, sublingual tablets, etc. can be provided.

Neat powders are manufactured by comminuting the active substance to size. Powders are manufactured by comminuting the active substance to size and admixing the resulting neat powder with a pharmaceutical excipient, such as an edible carbohydrate, e.g. starch, mannitol, etc., which has been similarly comminuted beforehand. If necessary, a corrigent, preservative, dispersant, colorant, perfume, etc. can also be incorporated.

Capsules can be manufactured by preparing neat or formulated powders in the above manner or granules in the manner described hereinafter for tablets and, then, filling gelatin or other capsule shells with the powders or granules. Prior to the filling operation, a lubricant or fluidizing agent, such as colloidal silica, talc, magnesium stearate, calcium stearate, solid polyethylene glycol, etc., can be added, each in finely divided state, to said granules. An improvement in effect of the drug administered may be obtained by adding a disintegrator or solubilizer, such as carboxymethylcellulose, carboxymethylcellulose calcium, low-substituted hydroxypropylcellulose, crosscarmelose sodium, carboxystarch sodium, calcium carbonate, sodium carbonate and so on.

Soft capsules can be obtained by suspending a finely divided powder of the drug in a mixture of vegetable oil, polyethylene glycol, glycerin and surfactant and sealing the suspension in a flexible gelatin shell. Tablets can be manufactured by preparing a powdery composition, processing it into granules or slags, and after addition of a disintegrator or lubricant, compression-molding the mixture. The powdery composition can be prepared by mixing the pulverized drug with said diluent and base, with or without addition of a binder (e.g. carboxymethylcellulose sodium, hydroxypropylcellulose, methylcellulose, hydroxypropylmethylcellulose, gelatin, polyvinylpyrrolidone, polyvinyl alcohol, etc.), a dissolution retardant (e.g. paraffin, wax, hydrogenated castor oil, etc.), a reabsorption agent (e.g. a quaternary salt) and/or an adsorbent (e.g. bentonite, kaolin, dicalcium phosphate, etc.). The powdery composition can be granulated by wetting it with a binder, such as a syrup, starch paste, gum arabic, a cellulose or polymer solution or the like and, then, passing it through a sieve by force. Instead of such a granulation process, the composition may first be tableted and the resulting slags of crude form are comminuted into granules.

To the granules which are manufactured in the above manner, an appropriate lubricant, such as stearic acid, stearates, talc, mineral oil, etc., can be added for preventing the interadhesion of individual granules. The thus lubricated composition is then compression-molded.

The bare tablets thus obtained can be film-coated or sugar-coated.

Instead of being processed through said granulation and slagging steps, the drug may be admixed with a free-flowing inert carrier and directly compression-molded. It is also possible to utilize a transparent or translucent protective coating consisting in a hermetically sealing shellac film, a sugar or polymeric coating or a polished wax coating.

Other oral dosage forms such as solutions, syrups and elixirs can also be provided in unit dosage forms so that the drug may be delivered in constant quantities. Syrups can be manufactured by dissolving the compound in an appropriate flavored aqueous medium, while elixers can be manufactured using a nontoxic alcoholic vehicle. Suspensions can be formulated by dispersing the compound in a nontoxic vehicle. Solubilizers and emulsifiers (e.g. ethoxylated isostearyl alcohol, polyoxyethylene sorbitol ester), preservatives, flavorants (e.g. peppermint oil, saccharin) and other agents can also be added, where necessary.

If necessary, such a unit dosage form for oral administration can be microencapsulated. The dosage unit may also be coated or embedded in a polymer, wax or the like for prolonged action or sustained release.

For administration into tissues, liquid unit dosage forms for subcutaneous, intramuscular or intravenous administration, such as solutions and suspensions, can be utilized. Thus, these preparations can be manufactured by suspending or dissolving a predetermined amount of the active compound in an injectable nontoxic liquid vehicle, such as an aqueous or oily medium, and sterilizing the resulting suspension or solution. An alternative procedure comprises filling vials with a predetermined amount of the active compound, sterilizing the filled vials and sealing them. For extemporaneous reconstitution or blending, there may be provided a spare vial and vehicle accompanying a powdered or lyophilized preparation of the active ingredient. For isotonization, a nontoxic salt or a solution of the salt may be added to an injectable composition. Moreover, stabilizers, preservatives, emulsifiers and the like may also be employed.

For rectal administration, suppositories can be provided by formulating the active compound with lower-melting water-soluble or -insoluble solid, such as polyethylene glycol, cacao butter or a higher ester (e.g. myristyl palmitate), or a mixture thereof.

For administration by inhalation, a vapor inhaler may be used. Alternatively, a pressure-resistant container or a nebulizer may be used in conjunction with a spray preparation or aerosol.

When a nebulizer is employed, the drug can be administered in mist form into the throat or nasal cavity by filling the nebulizer with a solution of the compound of the invention in an aqueous or oily vehicle, such as water, physiological saline or aqueous alcohol, and blowing air forcefully into the nebulizer. If necessary, auxiliary agents such as a solubilizer may be employed. The unit dose can be controlled by adjusting the air flow rate.

When a pressure-resistant container is employed, a liquefied gas or compressed gas propulsion system of the binary or ternary type (binary liquid phase, emulsion) or the suspension type can be formulated and topically administered in the mist, foam, jet or paste form into the throat or nasal cavity. The unit dose of such a spray preparation can be controlled by means of a metered dose valve.

BEST MODE OF CARRYING OUT THE INVENTION

The following reference examples, working examples, test examples, and examples of production of the compound of the invention are intended to describe the invention in further detail.

Reference Example 1

2-[3-[1-(1H-tetrazol-5-yl)ethoxy]phenoxy]aniline

Step 1 3-(2-Nitrophenoxy)anisole

To 150 ml of dimethyl sulfoxide were added 19.9 g of 3-methoxyphenol and 9.1 g of potassium hydroxide and the mixture was heated to 70°–80° C. to prepare a homogeneous solution. To this solution was added 21.1 g of 2-chloronitrobenzene and the mixture was stirred at 100° C. for 4 hours. The reaction mixture was then diluted with water and extracted with ether and the ether extract was washed succesively with 10% sodium hydroxide solution and saturated sodium chloride solution. The washed extract was dried over magnesium sulfate and the ether was distilled off to give 31.9 g of the title compound as a light yellow solid.

Step 2 3-(2-Nitrophenoxy)phenol

A mixture of 28.8 g of 3-(2-nitrophenoxy)anisole and 68 g of pyridine hydrochloride was heated to 160°–170° C. to prepare a homogeneous solution, which was further heated at 195°–205° C. with stirring for one hour. After cooling, the reaction mixture was diluted with water and extracted with ethyl acetate. The ethyl acetate layer was washed with water, dried and concentrated and the residue was subjected to silica gel and eluted with chloroform to give 23.8 g of the title compound as a light brown oil.

Step 3 Ethyl 2-[3-(2-nitrophenoxy)phenoxy]propionate

In 120 ml of acetone were dissolved 8.0 g of 3-(2-nitrophenoxy)phenol and 7.5 g of ethyl 2-bromopropionate followed by addition of 7.2 g of potassium carbonate. The mixture was refluxed for 5 hours and, after cooling, the insoluble matter was filtered off. The filtrate was concentrated to give 11.6 g of the title compound as a light brown oil.

Step 4 2-[3-(2-Nitrophenoxy)phenoxy]propionic acid

In 100 ml of ethanol was dissolved 6.7 g of ethyl 2-[3-(2-nitrophenoxy)phenoxy]propionate followed by addition of a solution of 1.6 g of sodium hydroxide in 10 ml of water, and the mixture was stirred at room temperature for 1 hour. The ethanol was then distilled off and the residue was diluted with water, acidified with hydrochloric acid and extracted with chloroform. The chloroform layer was dried and concentrated to give 6.2 g of the title compound as a light yellow oil.

Step 5 2-[3-(2-Nitrophenoxy)phenoxy]propionamide

In 100 ml of methylene chloride were dissolved 6.15 g of 2-[3-(2-nitrophenoxy)phenoxy]propionic acid and 4.2 g of triethylamine, followed by dropwise addition of 2.5 g of ethyl chloroformate at a temperature not exceeding 0° C., and the mixture was further stirred at the same temperature for 30 minutes. The reaction mixture was poured into previously ice-cooled methylene chloride (120 ml) saturated with ammonia gas and the mixture was then stirred at room temperature for 30 minutes. The methylene chloride layer was washed with water (twice), dried and concentrated and the residue was crystallized from methanol and isopropyl ether to give 3.3 g of the title compound.

Step 6 2-[3-(2-Nitrophenoxy)phenoxy]propionitrile

In a mixture of 12 ml of pyridine and 35 ml of dioxane was suspended 4.55 g of 2-[3-(2-nitrophenoxy)phenoxy]propionamide and, then, 3.6 g of trifluoroacetic anhydride was added dropwise with ice-cooling and stirring. The mixture was then stirred at that temperature for 30 minutes and, following addition of ice-water, extracted with ether. The ether extract was washed with diluted hydrochloric acid and sodium hydrogen carbonate solution in that order, dried and concentrated to give 4.3 g of the title compound as a light yellow oil.

Step 7 5-[1-[3-(2-Nitrophenoxy)phenoxy]ethyl]-1H-tetrazole

In 25 ml of N,N-dimethylformamide was dissolved 2.0 g of the 2-[3-(2-nitrophenoxy)phenoxy]propionitrile followed by addition of 0.92 g of sodium azide and 0.76 g of ammonium chloride, and the mixture was stirred at 115° C. for 80 minutes. The reaction mixture was then poured into ice-water containing 3 ml of concentrated hydrochloric acid and extracted with ethyl acetate. The ethyl acetate layer was washed with water, dried and concentrated to give 2.4 g of the title compound as a light brown oil.

Step 8 2-[3-[1-(1H-Tetrazol-5-yl)ethoxy]phenoxy]aniline

In 30 ml of ethanol was dissolved 5-[1-[3-(2-nitrophenoxy)phenoxy]ethyl]-1H-tetrazole and catalytic hydrogenation was carried out in the presence of 0.3 g of palladium-carbon at atmospheric temperature and pressure. After the reaction, the catalyst was filtered off and the filtrate was concentrated to give 2.1 g of the title compound as a brown oil.

2-[3-(1H-Tetrazol-5-ylmethoxy)phenoxy]aniline was produced in the same manner as Reference Example 1.

Reference Example 2

2-[3-(1H-Tetrazol-5-yl)phenoxy]aniline

Step 1 3-(2-Nitrophenoxy)benzonitrile

In 50 ml of N,N-dimethylformamide were dissolved 5.0 g of 3-cyanophenol and 5.93 g of 2-fluoronitrobenzene followed by addition of 8.71 g of potassium carbonate, and the mixture was stirred with heating at 100° C. for 2 hours. After cooling, the reaction mixture was diluted with water and extracted with ethyl acetate. The ethyl acetate layer was washed with water 3 times, dried and concentrated. The residue was crystallized from diisopropyl ether to give 9.63 g of the title compound as light yellow crystals.

Step 2 5-[3-(2-Nitrophenoxy)phenyl]-1H-tetrazole

In 40 ml of N,N-dimethylformamide was dissolved 4.0 g of 3-(2-nitrophenoxy)benzonitrile followed by addition of 2.28 g of sodium azide and 1.88 g of ammonium chloride, and the mixture was stirred at 110° C. for 4 hours. After cooling, the reaction mixture was acidified with diluted hydrochloric acid and extracted with ethyl acetate. The ethyl acetate layer was washed with water twice, dried and concentrated. The residue was crystallized from ethyl acetate-benzene to give 3.6 g of the title compound as light brown crystals.

Step 3 2-[3-(1H-Tetrazol-5-yl)phenoxy]aniline

In a mixture of 18 ml of ethanol and 9 ml of N,N-dimethylformamide was dissolved 1.5 g of 5-[3-(2-nitrophenoxy)phenyl]-1H-tetrazole and catalytic hydrogenation was carried out in the presence of 0.3 g of palladium-carbon at atmospheric temperature and pressure. After this reaction, the catalyst was filtered off and the filtrate was concentrated to give 1.3 g of the title compound as a colorless oil.

Reference Example 3

N-[2-[2-Cyanophenoxy]phenyl]-4-hexyloxybenzamide

Step 1 2-(2-Aminophenoxy)benzonitrile

In 50 ml of ethyl acetate was dissolved 2.5 g of 2-(2-nitrophenoxy)benzonitrile (prepared in accordance with Reference Example 2, Step 1) and catalytic hydrogenation was carried out in the presence of 0.5 g of palladium-carbon at atmospheric temperature and pressure. After the reaction, the catalyst was filtered off, the filtrate was concentrated and the residue was subjected to silica gel column chromatography using chloroform as the eluent to give 2.0 g of the title compound as a colorless oil.

Step 2
N-[2-[2-Cyanophenoxy]phenyl]-4-hexyloxybenzamide

In 20 ml of ether was dissolved 2.0 g of 2-(2-aminophenoxy)benzonitrile followed by addition of 2.04 g of triethylamine. Then, with ice-cooling and stirring, a solution of 2.67 g of 4-hexyloxybenzoyl chloride in 5 ml of ether was added dropwise. The mixture was further stirred at the same temperature for 1 hour. The reaction mixture was then washed with diluted hydrochloric acid and aqueous sodium hydrogen carbonate solution in that order, dried and concentrated. The residue was purified by silica gel column chromatography using ethyl acetate-n-hexane as the eluent and the relevant fraction was crystallized from diisopropyl ether to give 3.05 g of the title compound as white crystals.

Ethyl 4-[2-(4-cyanophenoxy)phenylcarbamoyl]-phenoxyacetate was produced in the same manner as Reference Example 3.

Reference Example 4

(E)-N-[2-(2-Cyanophenylthio)phenyl]-4-(2-heptenyloxy)benzamide

Step 1 Ethyl 2-(2-nitrophenylthio)benzoate

In 100 ml of N,N-dimethylformamide was dissolved 15.4 g of thiosalicylic acid followed by addition of 42 g of potassium carbonate and 14.8 g of 2-fluoronitrobenzene, and the mixture was stirred at 100° C. for 3 hours. After the reaction mixture had cooled to room temperature, 18.7 g of ethyl iodide was added thereto and the mixture was further stirred at room temperature for 3 hours. The reaction mixture was then poured into ice-water and extracted with ether. The ether layer was washed with water twice, dried and concentrated. Finally the residue was crystallized from ethanol to give 25.5 g of the title compound as yellow crystals.

Step 2 Ethyl 2-(2-aminophenylthio)benzoate

In 130 ml of ethanol was suspended 22.5 g of ethyl 2-(2-nitrophenylthio)benzoate and, then, a solution of 58.7 g of tin(IV) chloride dihydrate in a mixture of 70 ml of concentrated hydrochloric acid and 45 ml of ethanol was added en bloc. The mixture was stirred at room temperature for 3 hours, after which it was poured in a mixture of 600 ml of 10% aqueous sodium hydroxide solution and 500 ml of ether with cooling and stirring. The ether layer was separated, washed with water and saturated aqueous sodium chloride solution in that order and dried. Finally, the ether was distilled off to give 20.5 g of the title compound as a light yellow oil.

Step 3
(E)-2-[2-[4-(2-heptenyloxy)benzoylamino]phenylthio]-benzoic acid

In 30 ml of methylene chloride were dissolved 2.1 g of ethyl 2-(2-aminophenylthio)benzoate and 1.8 g of triethylamine, followed by dropwise addition of 2.2 g of (E)-4-(2-heptenyloxy)benzoyl chloride with ice-cooling and stirring. The mixture was stirred at room temperature for 10 hours, and then the methylene chloride was distilled off. The residue was diluted with water and extracted with ether. The ether layer was washed with diluted hydrochloric acid and saturated sodium hydrogen carbonate solution and dried and the ether was distilled off. The oily residue was dissolved in 50 ml of ethanol followed by addition of 7 ml of 10% aqueous sodium hydroxide solution, and the mixture was heated on a water bath for 40 minutes. After cooling, the reaction mixture was acidified with hydrochloric acid and diluted with water and the crystals separated out therefrom were collected by filtration and washed with water and aqueous ethanol in that order to give 2.8 g of the title compound as white crystals.

Step 4
(E)-2-[2-[4-(2-heptenyloxy)benzoylamino]phenylthio]-benzamide

In 40 ml of benzene was suspended 2.8 g of (E)-2-[2-[4-(2-heptenyloxy)benzoylamino]phenylthio]benzoic acid followed by addition of 1.2 g of N,N'-carbonyldiimidazole, and the mixture was stirred at room temperature for 2 hours. Ammonia gas was introduced into the mixture with ice-cooling and stirring for 20 minutes and the mixture was then allowed to stand at room temperature for 2 hours. The crystals separated out therefrom were collected by filtration and washed with ethyl acetate to give 2.6 g of the title compound as white crystals.

Step 5
(E)-N-[2-(2-Cyanophenylthio)phenyl]-4-(2-heptenyloxy)benzamide

In a mixture of 5 ml of pyridine and 50 ml of dioxane was suspended 2.5 g of (E)-2-[2-[4-(2-heptenyloxy)benzoylamino]phenylthio]benzamide followed by dropwise addition of 2.2 g of trifluoroacetic anhydride with ice-cooling and stirring.. After completion of dropwise addition, the mixture was stirred at room temperature for an additional 3 hours. Then, ice-water was added and the crystals separated out therefrom were collected by filtration, washed with water and dried to give 2.4 g of the title compound as white crystals.

In the same manner as Reference Example 4, the following compounds were produced.

N-[2-(3-Cyanomethylphenoxy)phenyl]-4-hexyloxybenzamide

N-[2-(2-Cyanomethylphenoxy)phenyl]-4-hexyloxybenzamide (E)-N-[3-Chloro-2-(2-cyanophenylthio)phenyl]-4-(2-heptenyloxy)benzamide (E)-N-[4-Methoxy-2-(2-cyanophenylthio)phenyl]-4-(2-heptenyloxy)benzamide N-[2-(2-Cyanophenylthio)phenyl]-4-(4-phenylbutoxy)-benzamide N-[3-Chloro-2-(2-cyanophenylthio)phenyl]-4-(4-phenylbutoxy)benzamide N-[2-(2-Cyanophenylthio)-3-fluorophenyl]-4-(4-phenylbutoxy)benzamide N-[2-(2-Cyanophenylthio)phenyl]-4-pentyloxybenzamide N-[2-(2-Cyanophenylthio)phenyl]-4-heptyloxybenzamide (E)-N-[2-(2-Cyanophenylthio)phenyl]-4-(2-hexenyloxy)benzamide

Reference Example 5

N-[2-(2-Cyanophenylthio)phenyl]-4-hexyloxybenzamide

Step 1 2-(2-Nitrophenylthio)benzoic acid

In 300 ml of N,N-dimethylformamide were suspended 30.8 g of thiosalicylic acid, 28.2 g of 2-fluoronitrobenzene and 69.0 g of potassium carbonate, and the mixture was stirred at 100° C. for 2 hours. After cooling, water was added and acidified with hydrochloric acid and the crystals separated out therefrom were collected by filtration and washed with water. The crystals were then dissolved in ethyl acetate and the solution was dried over magnesium sulfate and filtered. The filtrate was concentrated and the crystals separated out therefrom were collected by filtration and dried to give 42.6 g of the title compound as yellow prisms, m.p. 169°–171° C.

Step 2 2-(2-Nitrophenylthio)benzamide

In 200 ml of benzene were suspended 20.0 g of 2-(2-nitrophenylthio)benzoic acid and 40 ml of thionyl chloride and the suspension was refluxed for 6 hours. The solvent and the excess thionyl chloride were distilled off under reduced pressure, whereupon 22 g of 2-(2-nitrophenylthio)benzoyl chloride was obtained as yellow crystals. Without further purification, this product was dissolved in a mixture of 200 ml of ether and 100ml of methylene chloride and ammonia gas was bubbled through the solution with ice-cooling for 15 minutes. The mixture was then stirred at room temperature for 1 hour, after which crystals separated out therefrom were collected by filtration, washed with water and washed with hot ethanol to give 18.4 g of the title compound as light yellow crystals, m.p. 166°–167° C.

Step 3 2-(2-Nitrophenylthio)benzonitrile

In a mixture of 12.7 g of pyridine and 80 ml of dioxane was suspended 8.8 g of 2-(2-nitrophenylthio)benzamide, followed by dropwise addition of 10.1 g of trifluoroacetic anhydride with ice-cooling, and the mixture was stirred for 1 hour. To the reaction mixture was added water and the crystals separated out therefrom were collected by filtration, washed with water and hot ethanol and dried. The procedure gave 7.84 g of the title compound as yellow crystals, m.p. 166°–167° C.

Step 4 2-(2-Aminophenylthio)benzonitrile

In a mixture of 40 ml of concentrated hydrochloric acid, 60 ml of methanol and 40 ml of N,N-dimethylformamide was suspended 2-(2-nitrophenylthio)benzonitrile followed by addition of 8.64 g of powdered iron en bloc, and the mixture was stirred at 60° C. for 1 hour. The reaction mixture was then diluted with water and the precipitate was extracted with ether. This extract was washed with aqueous sodium hydrogen carbonate solution and water in that order and dried over magnesium sulfate. The solvent was then distilled off and the residue was subjected to column chromatography (Wakogel C200) using ethyl acetate-n-hexane (1:4) as the eluent. The crystals obtained were recrystallized from ethyl acetate-n-hexane to give 4.8 g of the title compound as white crystals, m.p. 86°–89° C.

Step 5

N-[2-(2-Cyanophenylthio)phenyl]-4-hexyloxybenzamide

In 2 ml of thionyl chloride was dissolved 1.03 g of 4-hexyloxybenzoic acid and the solution was refluxed for 1 hour. The excess thionyl chloride was distilled off and the residue was dried in vacuo to give 4-hexyloxybenzoyl chloride. Separately, 1.00 g of 2-(2-aminophenylthio)benzonitrile and 0.89 g of triethylamine were dissolved in 10 ml of ether and while the solution was stirred with ice-cooling, a solution of the above 4-hexyloxybenzoyl chloride in 5 ml of ether was added. The mixture was stirred overnight. Next morning, water and an aqueous solution of sodium hydrogen carbonate were added in the order mentioned and the resulting precipitate was extracted with ethyl acetate. The extract was dried over magnesium sulfate, the solvent was distilled off, and the residue was recrystallized from ethyl acetate-n-hexane to give 1.27 g of the title compound as white prisms.

In the same manner as Reference Example 5, the following compounds were produced.

(E)-N-[5-Chloro-2-(2-cyanophenylthio)phenyl]-4-(2-heptenyloxy)benzamide

N-[5-chloro-2-(2-cyanophenylthio)phenyl]-4-hexyloxybenzamide

Reference Example 6

Methyl 4-[2-(2-cyanophenylthio)phenylcarbamoyl]phenoxyacetate

Step 1

N-[2-(2-Cyanophenylthio)phenyl]-4-hydroxybenzamide

In 60 ml of ether were dissolved 2.6 g of 2-(2-aminophenylthio)benzonitrile (prepared in accordance with Reference Example 5, Step 4) and 2.8 g of pyridine, followed by dropwise addition of a solution of 2.7 g of 4-acetoxybenzoyl chloride in ether with ice-cooling and stirring. After completion of dropwise addition, the mixture was stirred at room temperature for 10 hours. The ether was then distilled off and ethanol was added to the residue. The resulting crystals were collected by filtration and washed with ethanol. The crystals were then suspended in 70 ml of ethanol, and after 7 ml of 10% aqueous sodium hydroxide solution was added, the mixture was stirred at room temperature for 1 hour. The reaction mixture was acidified with concentrated hydrochloric acid and diluted with water. The crystals separated out therefrom were collected by filtration and dried to give 3.3 g of the title compound as white crystals.

Step 2 Methyl 4-[2-(2-cyanophenylthio)phenylcarbamoyl]phenoxyacetate

In 10 ml of N,N-dimethylformamide were dissolved 1.0 g of N-[2-(2-cyanophenylthio)phenyl]-4-hydroxybenzamide and 0.49 g of methyl bromoacetate followed by addition of 0.6 g of potassium carbonate, and the mixture was stirred at room temperature for 4 hours. The reaction mixture was then diluted with water and crystals separated out therefrom were collected by filtration and washed with water and aqueous ethanol in that order to give 1.2 g of the title compound as white crystals.

In the same manner as Reference Example 6, the following compounds were produced.

N-[2-(2-Cyanophenylthio)phenyl]-4-(2-quinolylmethoxy)benzamide
N-[2-(2-Cyanophenoxy)phenyl]-4-(2-quinolylmethoxy)-benzamide
N-[2-(2-Cyanophenylthio)phenyl]-4-(7-chloro-2-quinolylmethoxy)benzamide
N-[2-(2-Cyanophenylthio)phenyl]-4-(6-hydroxyhexyloxy)benzamide
Ethyl 4-[4-[2-(2-cyanophenylthio)phenylcarbamoyl]phenoxy]butyrate
Ethyl 6-[4-[2-(2-cyanophenylthio)phenylcarbamoyl]phenoxy]hexanate
Ethyl 4-[2-(2-cyanophenoxy)phenylcarbamoyl]phenoxyacetate
N-[2-(2-Cyanophenylthio)phenyl]-4-heptyloxybenzamide
N-[2-(2-Cyanophenylthio)phenyl]-4-pentyloxybenzamide
N-[2-(2-Cyanophenylthio)phenyl]-4-(5-oxohexyloxy)-benzamide
N-[2-(2-Cyanophenylthio)phenyl]-4-cyanomethoxybenzamide
Ethyl 2-[4-[2-(2-cyanophenylthio)phenylcarbamoyl]phenoxy]propionate
Ethyl 2-methyl-2-[4-[2-(2-cyanophenylthio)phenylcarbamoyl]phenoxy]propionate
N-[2-(2-Cyanophenoxy)phenyl]-4-(6-hydroxyhexyloxy)benzamide
N-[2-(2-Cyanophenoxy)phenyl]-4-(5-oxohexyloxy)benzamide
Ethyl 4-[4-[2-(2-cyanophenoxy)phenylcarbamoyl]phenoxy]butyrate
Ethyl 6-[4-[2-(2-cyanophenoxy)phenylcarbamoyl]phenoxy]hexanate

Reference Example 7

2-[2-(1H-Tetrazol-5-yl)phenylthio]aniline

In 25 ml of DMF were suspended 2.4 g of 2-(2-aminophenylthio)benzonitrile (prepared in accordance with Reference Example 5, Step 4), 3.4 g of sodium azide and 1.7 g of ammonium chloride and the suspension was stirred at 110°–120° C. for 5 hours. After cooling, the reaction mixture was diluted with water, acidified with acetic acid and extracted with ethyl acetate. The extract was washed with water, dried and concentrated and the residue was crystallized from ethyl acetate and isopropyl ether to give 1.9 g of the title compound as white crystals, m.p. 153°–156° C.

In the same manner as Reference Example 7, the following compounds were produced.
5-Chloro-2-[2-(1H-tetrazol-5-yl)phenylthio]aniline
5-Methoxy-2-[2-(1H-tetrazol-5-yl )phenylthio]aniline
3-Fluoro-2-[2-(1H-tetrazol-5-yl)phenylthio]aniline
5-Methyl-2-[2-(1H-tetrazol-5-yl)phenylthio]aniline
2-[2-(1H-Tetrazol-5-yl)phenylthio]-5-trifluoromethylaniline
5-Fluoro-2-[2-(1H-tetrazol-5-yl)phenylthio]aniline
4-Methyl-2-[2-(1H-tetrazol-5-yl)phenylthio]aniline
3-Chloro-2-[2-(1H-tetrazol-5-yl )phenylthio]aniline
4-[2-(1H-Tetrazol-5-yl)phenylthio]aniline
2-[4-(1H-Tetrazol-5-yl)phenylthio]aniline
2-[3-Chloro-2-(1H-tetrazol-5-yl)phenylthio]aniline
2-[4-Chloro-2-(1H-tetrazol-5-yl)phenylthio]aniline
2-[3-Methoxy-2-(1H-tetrazol-5-yl)phenylthio]aniline
2-[5-Methoxy-2-(1H-tetrazol-5-yl)phenylthio]aniline
2-[3-Methyl-2-(1H-tetrazol-5-yl )phenylthio]aniline
4-Chloro-2-[2-(1H-tetrazol-5-yl)phenylthio]aniline
4-Methoxy-2-[2-(1H-tetrazol-5-yl)phenylthio]aniline
4-Hydroxy-2-[2-(1H-tetrazol-5-yl)phenylthio]aniline
5-Hydroxy-2-[2-(1H-tetrazol-5-yl)phenylthio]aniline
2-[2-(1H-tetrazol-5-yl)phenylthio]-N-methylaniline

Reference Example 8

N-[2-(2-Cyanophenylthio)phenyl]-4-(5-hydroxyhexyloxy)benzamide

In 30 ml of tetrahydrofuran was suspended 3.33 g of N-[2-(2-cyanophenylthio)phenyl]-4-(5-oxohexyloxy)b-enz-amide (prepared in accordance with Reference Example 6, Step 2) followed by addition of a solution of 0.31 g of sodium borohydride in methanol, and the mixture was stirred for 1 hour. To the reaction mixture was added chloroform and the mixture was washed with saturated aqueous sodium chloride solution, dried over magnesium sulfate and concentrated. The residue was recrystallized from ethyl acetate-n-hexane to give 3.15 g of the title compound as white crystals.

In the same manner as Reference Example 8, the following compound was produced.
N-[2-(2-Cyanophenoxy)phenyl]-4-(5-hydroxyhexyloxy)benzamide

Reference Example 9

Ethyl 4-[2-(2-cyanophenylsulfinyl)phenylcarbamoyl]phenoxyacetate

To a solution of 1.51 g of ethyl 4-[2-(2-cyanophenylthio)phenylcarbamoyl]phenoxyacetate (prepared in accordance with Reference Example 6, Step 2) in 5 ml of chloroform was added dropwise a solution of 0.87 g of 70% m-chloroperbenzoic acid in 20 ml of chloroform and the mixture was stirred at room temperature for 2 hours. The reaction mixture was then washed with aqueous sodium hydrogen carbonate solution and dried over magnesium sulfate and the solvent was distilled off. The residue was recrystallized from ethyl acetate-n-hexane to give 1.3 g of the title compound as white crystals, m.p. 128°–130° C. .

In the same manner as Reference Example 9, the following compounds were produced.
Ethyl 4-[4-[2-(2-cyanophenylsulfinyl)phenylcarbamoyl]phenoxy]butyrate
Ethyl 6-[4-[2-(2-cyanophenylsulfinyl)phenylcarbamoyl]phenoxy]hexanate
N-[2-(2-Cyanophenylsulfinyl)phenyl]-4-(6-hydroxyhexyloxy)benzamide
N-[2-(2-Cyanophenylsulfinyl)phenyl]-4-(5-hydroxyhexyloxy)benzamide

Reference Example 10

Ethyl 4-[2-(2-cyanophenylsulfonyl)phenylcarbamoyl]phenoxyacetate

To a solution of 1.51 g of ethyl 4-[2-(2-cyanophenylthio)phenylcarbamoyl]phenoxyacetate (prepared in accordance with Reference Example 6, Step 2) in 5 ml of chloroform was added dropwise a solution of 1.73 g of 70% m-chloroperbenzoic acid in 30 ml of chloroform and the mixture was stirred at room temperature overnight. The reaction mixture was then washed with aqueous sodium hydrogen carbonate solution and dried over magnesium sulfate and the solvent was distilled off. The residue was recrystallized from ethyl acetate-n-hexane to give 1.51 g of the title compound as white crystals, m.p. 131°–132° C.

In the same manner as Reference Example 10, the following compounds were produced.

Ethyl 4-[4-[2-(2-cyanophenylsulfonyl)phenylcarbamoyl]phenoxy]butyrate
Ethyl 6-[4-[2-(2-cyanophenylsulfonyl)phenylcarbamoyl]phenoxy]hexanate
N-[2-(2-Cyanophenylsulfonyl)phenyl]-4-(6-hydroxyhexyloxy)benzamide
N-[2-(2-Cyanophenylsulfonyl)phenyl]-4-(5-hydroxyhexyloxy)benzamide

Reference Example 11

An Alternative Process For Producing 2-(2-Aminophenylthio)Benzonitrile (the Product According to Reference Example 5, Step 4)

In 10 ml of DMF was dissolved 1.25 g of orthoaminothiophenol followed by addition of 1.38 g of potassium carbonate. The mixture was preheated at 100° C. and after 1.45 g of o-chlorobenzonitrile was added, the mixture was stirred in an argon gas stream at 100° C. for 1 hour. To the reaction mixture was added ice-water and the mixture was extracted with ethyl acetate. The extract was washed with water twice and dried over magnesium sulfate and the solvent was distilled off. The residue was crystallized from n-hexane-isopropyl ether to give 1.91 g of the title compound as white crystals, m.p. 88°–90° C.

In the same manner as Reference Example 11, the following compounds were produced.
2-(2-Aminophenylthio)-6-chlorobenzonitrile
2-(2-Aminophenylthio)-5-chlorobenzonitrile
2-(2-Aminophenylthio)-6-methoxybenzonitrile
2-(2-Aminophenylthio)-4-methoxybenzonitrile
2-(2-Aminophenylthio)-6-methylbenzonitrile

Reference Example 12

3-(2-Aminophenylthio)-2-(1H-tetrazol-5-yl)phenol

In 14 ml of 1.4M sodium ethylthiolate in N,N-dimethylformamide was dissolved 0.6 g of 2-[3-methoxy-2-(1H-tetrazol-5-yl)phenylthio]aniline (prepared by the process described in Reference Example 7) and the solution was refluxed for 6 hours. To the reaction mixture was added ice-water and the mixture was acidified weakly with diluted hydrochloric acid and extracted with ether. The ether layer was washed with water, dried over magnesium sulfate and concentrated. The residue was subjected to silica gel column chromatography using 5% methanol-chloroform as the eluent to give 0.2 g of the title compound as white crystals, m.p. 220°–225° C. (decomp.)

In the same manner as Reference Example 12, the following compound was produced.
3-(2-Aminophenylthio)-4-(1H-tetrazol-5-yl)phenol

Reference Example 13

2-[2-(Methylamino)phenylthio]benzonitrile

Step 1
2-[2-(Trifluoroacetylamino)phenylthio]benzonitrile

In 25 ml of methylene chloride were dissolved 2.3 g of 2-(2-aminophenylthio)benzonitrile (prepared in accordance with Reference Example 5, Step 4) and 1.1 g of triethylamine, followed by dropwise addition of 2.2 g of trifluoroacetic anhydride with ice-cooling and stirring. After completion of dropwise addition, the mixture was stirred with ice-cooling for 2 hours, after which the solvent was distilled off and the residue was crystallized from 50% aqueous ethanol to give 2.8 g of the title compound as white crystals.

Step 2
2-[2-(N-Methyl-N-trifluoroacetylamino)phenylthio]benzonitrile

In 20 ml of N,N-dimethylformamide was dissolved 2.8 g of 2-[2-(trifluoroacetylamino)phenylthio]benzonitrile followed by addition of 2.4 g of methyl iodide and 2.4 g of potassium carbonate, and the mixture was stirred at room temperature for 2 hours, at the end of which time the reaction mixture was diluted with water. The crystals separated out therefrom were collected by filtration, washed with water and aqueous ethanol to give 2.8 g of the title compound as white crystals.

Step 3 2-[2-(Methylamino)phenylthio]benzonitrile

In 20 ml of ethanol was suspended 2.8 g of 2-[2-(N-methyl-N-trifluoroacetylamino)phenylthio]benzonitrile followed by addition of 4 ml of 10% aqueous sodium hydroxide solution, and the mixture was heated on a water bath for 5 minutes. After cooling, the crystals were collected by filtration and washed with 50% aqueous ethanol to give 1.8 g of the title compound as white crystals.

Example 1

N-[2-[3-[1-(1H-Tetrazol-5-yl)ethoxy]phenoxy]phenyl]-4-hexyloxybenzamide

In 30 ml of methylene chloride were dissolved 2.1 g of 2-[3-[1-(1H-tetrazol-5-yl)ethoxy]phenoxy]aniline and 2.2 g of triethylamine, followed by dropwise addition of a solution of 1.7 g of 4-hexyloxybenzoyl chloride in benzene with ice-cooling and stirring. The mixture was stirred at room temperature overnight and refluxed for 1 hour. To the reaction mixture was added ice-water and after the mixture was acidified with diluted hydrochloric acid, the methylene chloride layer was separated. The methylene chloride solution was dried over magnesium sulfate and concentrated and the oily residue was subjected to silica gel column chromatography using chloroform-methanol (100:1) as the eluent to give 2.2 g of the title compound as a light yellow oil.

Nuclear magnetic resonance spectrum (CDCl$_3$) 0.7–1.9 (14H, m), 3.91 (2H, t, J=6 Hz), 5.70 (1H, q, J=7 Hz), 6.4–7.3 (10H, m), 7.56 (2H, d, J=9 Hz), 8.1–8.4 (2H, m), 11 (1H, br).

Example 2

N-[2-[3-[1-(1H-tetrazol-5-yl)ethoxy]-phenoxy]phenyl]-4-hexyloxybenzamide sodium salt In 30 ml of ether was dissolved 2.0 g of N-[2-[3-[1-(1H-tetrazol-5-yl)ethoxy]phenoxy]phenyl]-4-hexyloxybenzamide followed by addition of a solution of 90 mg of sodium in ethanol, and the mixture was concentrated in vacuo to dryness. After addition of isopropyl ether, the resulting foamy solid was pulverized, filtered and dried to give 1.9 g of the sodium salt as a white amorphous powder.

Elemental analysis for $C_{28}H_{30}N_5O_4NaH_2O$ Calcd. (%) C:62.10 H:5.96 N:12.93 Found (%) C:62.54 H:6.57 N:13.09.

Example 3

N-[2-[3-(1H-Tetrazol-5-yl)methoxyphenoxy]phenyl]-4-hexyloxybenzamide

In 15 ml of N,N-dimethylformamide (DMF) was dissolved 1.5 g of N-[2-(3-cyanomethoxyphenoxy)-phenyl]-4-hexyloxybenzamide followed by addition of 0.44 g of sodium azide and 0.37 g of ammonium chloride, and the mixture was stirred at 105°–110° C. for 1 hour. After cooling, the reaction mixture was diluted with ice-water and acidified with hydrochloric acid. The resulting precipitate was collected by filtration and recrystallized from ethanol to give 1.35 g of the title compound as white crystals, m.p. 158°–159° C.

Elemental analysis for $C_{27}H_{29}N_5O_4$ Calcd. (%) C:66.51 H:6.00 N:14.36 Found (%) C:66.67 H:6.20 N:14.42.

Example 4

N-[2-[2-(1H-Tetrazol-5-yl)phenylthio]phenyl]-4-(4-phenylbutoxy)benzamide

In 20 ml of DMF were dissolved 1.35 g of N-[2-(2-cyanophenylthio)phenyl]-4-(4-phenylbutoxy)benzamide, 0.55 g of sodium azide and 0.46 g of ammonium chloride, and the mixture was stirred at 110°–115° C. for 5 hours. Then, 0.18 g of sodium azide and 0.15 g of ammonium chloride were further added and the mixture was stirred at 110° to 115° C. for 2 hours. After addition of ice-water, the reaction mixture was neutralized with diluted hydrochloric acid and the precipitate was collected by filtration and recrystallized from ethanol to give 0.95 g of the title compound, m.p. 156°–159° C.

Elemental analysis for $C_{30}H_{27}N_5O_2S$ Calcd. (%) C:69.08 H:5.22 N:13.43 Found (%) C:68.93 H:5.45 N:13.32.

Example 5

Methyl 4-[2-[2-(1H-tetrazol-5-yl)phenylthio]phenylcarbamoyl]phenoxyacetate

In 10 ml of DMF were suspended 1.1 g of methyl 4-[2-(2-cyanophenylthio)phenylcarbamoyl]phenoxyacetate, 0.85 g of sodium azide and 0.7 g of ammonium chloride, and the mixture was Stirred at 110°–120° C. for 8 hours. After cooling, the reaction mixture was acidified with concentrated hydrochloric acid and diluted with water. The resulting precipitate was subjected to silica gel column chromatography (chloroform→chloroform-ethanol=50:1) to give 0.4 g of the title compound as white crystals, m.p. 204°–205° C.

Elemental analysis for $C_{23}H_{19}N_5O_4S$ Calcd. (%) C:59.86 H:4.15 N:15.18 Found (%) C:59.95 H:4.23 N:15.22.

IR $cm^{-1}$ (KBr): 3380, 3100–2200, 1760, 1680, 1600 1580, 1500, 1440, 1300, 1220.

Example 6

4-[2-[2-(1H-Tetrazol-5-yl)phenylthio]phenylcarbamoyl]phenoxyacetic acid

In 10 ml of ethanol was suspended 0.38 g of methyl 4-[2-[2-(1H-tetrazol-5-yl)phenylthio]phenylcarbamoyl]-p-henoxyacetate followed by addition of 1 ml of 10% sodium hydroxide, and the mixture was heated on a water bath for 10 minutes. After cooling, the reaction mixture was acidified with concentrated hydrochloic acid and diluted with water. The precipitate was collected by filtration and washed with water, ethanol and ethyl acetate in the order mentioned to give 0.32 g of the title compound as white crystals, m.p. 252°–253° C.

Elemental analysis for $C_{22}H_{17}N_5O_4S$ Calcd. (%) C:59.05 H:3.83 N:15.65 Found (%) C:58.93 H:4.06 N:15.43.

Example 7

N-[2-[2-(1H-Tetrazol-5-yl)phenylthio]phenyl]-4-hexyloxybenzamide

In 20 ml of DMF was dissolved 1.20 g of N-[2-(2-cyanophenylthio)phenyl]-4-hexyloxybenzamide followed by addition of 0.36 g of sodium azide and 0.30 g of ammonium chloride, and the mixture was stirred at 120° C. for 3 hours. Then, the same amounts of sodium azide and ammonium chloride as above were added twice at an interval of 3 hours. The reaction mixture was then acidified with diluted hydrochloric acid and the resulting crystals were collected by filtration and washed with water. The crystals were dissolved in chloroform and dried over magnesium sulfate and the solvent was distilled off. The crystals thus obtained were recrystallized from ethyl acetate-n-hexane to give 1.1 g of the title compound as white crystals, m.p. 154°–156° C.

Elemental analysis for $C_{26}H_{27}N_5O_2S$ Calcd. (%) C:65.94 H:5.75 N:14.79 Found (%) C:66.01 H:6.03 N:14.78.

Example 8

N-[2-[2-(1H-Tetrazol-5-yl)phenylsulfinyl]phenyl]-4-hexyloxybenzamide

To a solution of 2.5 g of N-[2-[2-(1H-tetrazol-5yl)-phenylthio]phenyl]-4-hexyloxybenzamide in 30 ml of chloroform was added 1.5 g of 80% m-chloroperbenzoic acid, and the mixture was stirred at room temperature for 2 hours, at the end of which time the solvent was distilled off. Then, ethyl acetate-chloroform was added to the residue and the resulting crystals were collected by filtration and recrystallized from ethanol-chloroform to give 0.67 g of the title compound as white crystals, m.p. 206°–210° C. (decomp.)

Elemental analysis for $C_{26}H_{27}N_5O_3S \cdot \frac{1}{4} H_2O$ Calcd. (%) C:63.20 H:5.61 N:14.17 Found (%) C:63.12 H:5.74 N:14.25.

Example 9

N-[2-[2-(1H-Tetrazol-5-yl)phenylsulfonyl]phenyl]-4-hexyloxybenzamide

To a solution of 2.0 g of N-[2-[2-(1H-tetrazol-5-yl)phenylthio]phenyl]-4-hexyloxybenzamide in 20 ml of chloroform was added 2.0 g of 80% m-chloroperbenzoic acid and the mixture was stirred at room temperature for 20 hours. The crystals separated out therefrom were washed with chloroform and recrystallized from ethanol-chloroform to give 1.44 g of the title compound as white crystals, m.p. 203°–205° C. (decomp.)

Elemental analysis for $C_{26}H_{27}N_5O_4S$ Calcd. (%) C:61.77 H:5.38 N:13.85 Found (%) C:61.57 H:5.42 N:13.67.

In the same manner as above, the following compounds were obtained.

Example 10

N-[2-[3-(1H-Tetrazol-5-yl)methoxyphenoxy]phenyl]-4-heptyloxybenzamide

Melting point: 154°–156° C. Elemental analysis for $C_{28}H_{31}N_5O_4$ Calcd. (%) C:67.05 H:6.23 N:13.96 Found (%) C:67.04 H:6.46 N:13.67.

Example 11

N-[2-[3-(1H-Tetrazol-5-yl)phenoxy]phenyl]-4-hexyloxybenzamide

Melting point: 172°–173° C. Elemental analysis for $C_{26}H_{27}N_5O_3$ Calcd. (%) C:68.25 H:5.95 N:15.31 Found (%) C:68.38 H:5.94 N:15.34.

Example 12

N-[2-[3-(1H-Tetrazol-5-yl)methylphenoxy]phenyl]-4-hexyloxybenzamide

Melting point: 99°–104° C. Elemental analysis for $C_{27}H_{29}N_5O_3$ Calcd. (%) C:68.77 H:6.20 N:14.85 Found (%) C:68.75 H:6.38 N:14.70.

Example 13

N-[2-[2-(1H-Tetrazol-5-yl)methylphenoxy]phenyl]-4-hexyloxybenzamide

Melting point: 142°–143° C. Elemental analysis for $C_{27}H_{29}N_5O_3$ Calcd. (%) C:68.77 H:6.20 N:14.85 Found (%) C:68.76 H:6.25 N:14.61.

Example 14

(E)-N-[2-[2-(1H-Tetrazol-5-yl)phenylthio]phenyl]-4-(2-heptenyloxy)benzamide

Melting point: 154°–155° C. Elemental analysis for $C_{27}H_{27}N_5O_2S$ Calcd. (%) C:66.78 H:5.60 N:14.42 Found (%) C:66.82 H:5.54 N:14.31.

Example 15

(E)-N-[3-Chloro-2-[2-(1H-tetrazol-5-yl)phenylthio]phenyl]-4-(2-heptenyloxy)benzamide Melting point: 149°–150° C. Elemental analysis for $C_{27}H_{26}ClN_5O_2S$ Calcd. (%) C:62.36 H:5.04 N:13.47 Found (%) C:62.14 H:5.49 N:13.04.

Example 16

(E)-N-[5-Chloro-2-[2-(1H-tetrazol-5-yl)phenylthio]phenyl]-4-(2-heptenyloxy)benzamide Melting point: 187°–188° C. Elemental analysis for $C_{27}H_{26}ClN_5O_2S$ Calcd. (%) C:62.36 H:5.04 N:13.47 Found (%) C:62.31 H:5.08 N:13.38.

Example 17

(E)-N-[4-Methoxy-2-[2-(1H-tetrazol-5-yl)phenylthio]phenyl]-4-(2-heptenyloxy)benzamide Melting point: 156°–158° C. Elemental analysis for $C_{28}H_{29}N_5O_2S$ Calcd, (%) C:65.22 H:5.67 N:13.58 Found (%) C:65.22 H:5.64 N:13.20.

Example 18

N-[3-Chloro-2-[2-(1H-tetrazol-5-yl)phenylthio]phenyl]-4-(4-phenylbutoxy)benzamide Melting point: 145°–147° C. Elemental analysis for $C_{30}H_{26}ClN_5O_2S \cdot \frac{1}{2}H_2O$ Calcd, (%) C:63.76 H:4.82 N:12.39 Found (%) C:63.50 H:4.75 N:12.07.

Example 19

N-[3-Fluoro-2-[2-(1H-tetrazol-5-yl)phenylthio]phenyl]-4-(4-phenylbutoxy)benzamide Melting point: 175°–177° C. Elemental analysis for $C_{30}H_{26}FN_5O_2S$ Calcd. (%) C:66.77 H:4.86 N:12.98 Found (%) C:66.93 H:4.89 N:12.51.

Example 20

N-[2-[2-(1H-Tetrazol-5-yl)phenylthio]phenyl]-4-pentyloxybenzamide

Melting point: 170°–171° C. Elemental analysis for $C_{25}H_{25}N_5O_2S$ Calcd. (%) C:65.34 H:5.48 N:15.24 Found (%) C:65.46 H:5.49 N:15.00.

Example 21

N-[5-Chloro-2-[2-(1H-tetrazol-5-yl)phenylthio]phenyl]-4-hexyloxybenzamide

Melting point: 191°–193° C. Elemental analysis for $C_{26}H_{26}ClN_5O_2S$ Calcd. (%) C:61.47 H:5.16 N:13.79 Found (%) C:61.51 H:5.39 N:13.69.

Example 22

N-[2-[2-(1H-Tetrazol-5-yl)phenylthio]phenyl]-4-heptyloxybenzamide

Melting point: 157°–158° C. Elemental analysis for $C_{27}H_{29}N_5O_2S$ Calcd. (%) C:66.50 H:5.99 N:14.36 Found (%) C:66.66 H:5.84 N:14.26.

Example 23

(E)-N-[2-[2-(1H-Tetrazol-5-yl)phenylthio]phenyl]-4-(2-hexenyloxy)benzamide

Melting point: 177°–178° C. Elemental analysis for $C_{26}H_{25}N_5O_2S$ Calcd. (%) C:66.22 H:5.34 N:14.85 Found (%) C:66.39 H:5.42 N:14.91.

Example 24

N-[2-[2-(1H-Tetrazol-5-yl)phenoxy]phenyl]-4-hexyloxybenzamide

Melting point: 159°–161° C. Elemental analysis for $C_{26}H_{27}N_5O_3$ Calcd. (%) C:68.25 H:5.95 N:15.31 Found (%) C:68.55 H:6.22 N:15.20.

Example 25

N-[2-[2-(1H-Tetrazol-5-yl)phenylthio]phenyl]-4-(quinolin-2-ylmethoxy)benzamide

Melting point: 198°–200° C. Elemental analysis for $C_{30}H_{22}N_6O_2S$ Calcd. (%) C:67.91 H:4.18 N:15.84 Found (%) C:67.86 H:4.49 N:15.70.

Example 26

N-[2-[2-(1H-Tetrazol-5-yl)phenoxy]phenyl]-4-(quinolin-2-ylmethoxy)benzamide

Melting point: 224°–226° C. Elemental analysis for $C_{30}H_{22}N_6O \cdot \frac{1}{4}H_2O$ Calcd. (%) C:69.42 H:4.37 N:16.19 Found (%) C:69.50 H:4.76 N:15.82.

Example 27

N-[2-[2-(1H-Tetrazol-5-yl)phenylthio]phenyl]-4-(7-chloroquinolin-2-ylmethoxy)benzamide Melting point: 224°–226° C. Elemental analysis for $C_{30}H_{21}ClN_6O_2S$ Calcd. (%) C:63.77 H:3.75 N:14.87 Found (%) C:63.33 H:3.77 N:14.59.

Example 28

4-[4-[2-[2-(1H-Tetrazol-5-yl)phenylthio]phenylcarbamoyl]phenoxy]butyric acid

Melting point: 188° C. Elemental analysis for $C_{24}H_{21}N_5O_4S$ Calcd. (%) C:60.62 H:4.45 N:14.73 Found (%) C:60.65 H:4.71 N:14.78.

Example 29

N-[2-[2-(1H-Tetrazol-5-yl)phenylthio]phenyl]-4-(6-hydroxyhexyloxy)benzamide

Melting point: 192°–193° C. Elemental analysis for $C_{26}H_{27}N_5O_3S$ Calcd. (%) C:63.78 H:5.56 N:14.30 Found (%) C:63.76 H:5.51 N:14.23.

Example 30

4-[2-[2-(1H-Tetrazol-5-yl)phenoxy]phenylcarbamoyl]phenoxyacetic acid

Melting point: 123°–125° C. Elemental analysis for $C_{22}H_{17}N_5.\frac{1}{2}H_2O$ Calcd. (%) C:59.99 H:4.12 N:15.90 Found (%) C:60.23 H:4.20 N:15.94.

Example 31

6-[4-[2-[2-(1H-Tetrazol-5-yl)phenylthio]phenylcarbamoyl]phenoxy]hexanoic acid

Melting point: 185°–186° C. Elemental analysis for $C_{26}H_{25}N_5O_4S$ Calcd. (%) C:62.01 H:5.00 N:13.91 Found (%) C:61.97 H:4.97 N:13.84.

Example 32

Ethyl 4-[4-[2-[2-(1H-tetrazol-5-yl)phenylthio]phenylcarbamoyl]phenoxy]butyrate

Melting point: 173°–175° C. IR cm$^{-1}$(KBr): 3375, 3100–2300, 1735, 1680, 1600, 1580, 1500, 1435, 1250.

Example 33

Ethyl 6-[4-[2-[2-(1H-Tetrazol-5-yl)phenylthio]phenylcarbamoyl]phenoxy]hexanate

Melting point: 137°–138° C. IR cm$^{-1}$ (KBr): 3380, 3200–2300, 1730, 1680, 1600, 1575, 1500, 1435, 1245.

Example 34

N-[2-[2-(1H-Tetrazol-5-yl)phenoxy]phenyl]-4-(6-hydroxyhexyloxy)benzamide

Melting point: 174°–175° C. Elemental analysis for $C_{26}H_{27}N_5O_4$ Calcd. (%) C:65.95 H:5.75 N:14.79 Found (%) C:66.01 H:5.64 N:14.91.

Example 35

6-[4-[2-[2-(1H-Tetrazol-5-yl)phenoxy]phenylcarbamoyl]phenoxy]hexanoic acid

Melting point: 153°–154° C. Elemental analysis for $C_{26}H_{25}N_5O_5$ Calcd. (%) C:64.32 H:5.19 N:14.42 Found (%) C:63.99 H:5.22 N:14.32.

Example 36

4-[4-[2-[2-(1H-Tetrazol-5-yl)phenoxy]phenylcarbamoyl]phenoxybutyric acid

Melting point: 197°–198° C. Elemental analysis for $C_{24}H_{21}N_5O_5$ Calcd. (%) C:62.74 H:4.61 N:15.24 Found (%) C:62.82 H:4.75 N:15.11.

Example 37

N-[2-[2-(1H-Tetrazol-5-yl)phenoxy]phenyl]-4-(5-hydroxyhexyloxy)benzamide.

Melting point: 142°–144° C. Elemental analysis for $C_{26}H_{27}N_5O_4.\frac{1}{4}H_2O$ Calcd. (%) C:65.33 H:5.80 N:14.65 Found (%) C:65.39 H:5.75 N:14.59.

Example 38

N-[2-[2-(1H-Tetrazol-5-yl)phenylthio]phenyl]-4-(5-hydroxyhexyloxy)benzamide

Melting point: 161°–163° C. Elemental analysis for $C_{26}H_{27}N_5O_3S$ Calcd. (%) C:63.78 H:5.56 N:14.30 Found (%) C:63.40 H:5.56 N:14.04.

Example 39

N-[2-[2-(1H-Tetrazol-5-yl)phenylsulfinyl]phenyl]-4-(6-hydroxyhexyloxy)benzamide

Melting point: 196°–198° C. Elemental analysis for $C_{26}H_{27}N_3O_4S$ Calcd. (%) C:61.77 H:5.38 N:13.85 Found (%) C:61.63 H:5.45 N:13.87.

Example 40

6-[4-[2-[2-(1H-Tetrazol-5-yl)phenylsulfinyl]phenylcarbamoyl]phenoxy]hexanoic acid Melting point: 235°–236° C. (decomp.) Elemental analysis for $C_{26}H_{25}N_5O_5S$ Calcd. (%) C:60.10 H:4.85 N:13.48 Found (%) C:59.70 H:4.82 N:13.24.

Example 41

4-[4-[2-[2-(1H-Tetrazol-5-yl)phenylsulfinyl]phenylcarbamoyl]phenoxy]butyric acid Melting point: 254°–255° C. (decomp.) Elemental analysis for $C_{24}H_{21}N_5O_5S.\frac{1}{4} H_2O$ Calcd. (%) C:58.11 H:4.37 N:14.12 Found (%) C:58.02 H:4.31 N:14.20.

Example 42

4-[2-[2-(1H-Tetrazol-5-yl)phenylsulfinyl]phenylcarbamoyl]phenoxyacetic acid

Melting point: 272°–274° C. (decomp.) Elemental analysis for $C_{22}H_{17}N_5O_5S.\frac{1}{4}H_2O$ Calcd. (%) C:56.47 H:3.77 N:14.97 Found (%) C:56.45 H:3.95 N:15.04.

Example 43

N-[2-[2-(1H-Tetrazol-5-yl)phenylsulfinyl]phenyl]-4-(5-hydroxyhexyloxy)benzamide

Melting point: 195°–198° C. Elemental analysis for $C_{26}H_{27}N_5O_4S.\frac{1}{4}H_2O$ Calcd. (%) C:61.22 H:5.43 N:13.73 Found (%) C:61.16 H:5.48 N:13.76.

Example 44

N-[2-[2-(1H-Tetrazol-5-yl)phenylsulfonyl]phenyl]-4-(6-hydroxyhexyloxy)benzamide

Melting point: 182°–184° C. Elemental analysis for $C_{26}H_{27}N_5O_5S$ Calcd. (%) C:59.87 H:5.22 N:13.43 Found (%) C:59.76 H:5.38 N:13.13.

Example 45

6-[4-[2-[2-(1H-Tetrazol-5-yl)phenylsulfonyl]phenylcarbamoyl]phenoxy]hexanoic acid Melting point: 219°–221° C. Elemental analysis for $C_{26}H_{25}N_5O_6S$ Calcd. (%) C:58.31 H:4.70 N:13.08 Found (%) C:58.22 H:4.69 N:12.98.

Example 46

4-[4-[2-[2-(1H-Tetrazol-5-yl)phenylsulfonyl]phenylcarbamoyl]phenoxy]butyric acid Melting point: 238°–239° C. (decomp.) Elemental analysis for $C_{24}H_{21}N_5O_6S$ Calcd. (%) C:56.80 H:4.17 N:13.80 Found (%) C:56.76 H:4.08 N:14.06.

Example 47

4-[2-[2-(1H-Tetrazol-5-yl)phenylsulfonyl]phenylcarbamoyl]phenoxyacetic acid

Melting point: 222°–224° C. (decomp.) Elemental analysis for $C_{22}H_{17}N_5O_6S$ Calcd. (%) C:55.11 H:3.57 N:14.61 Found (%) C:54.97 H:3.55 N:14.40.

Example 48

N-[2-[2-(1H-Tetrazol-5-yl)phenylsulfonyl]phenyl]-4-(5-hydroxyhexyloxy)benzamide

Melting point: 170°–171° C. Elemental analysis for $C_{26}H_{27}N_5O_5S$ Calcd. (%) C:59.87 H:5.22 N:13.43 Found (%) C:59.74 H:5.35 N:13.28.

Example 49

4-[2-[4-(1H-Tetrazol-5-yl)phenoxy]phenylcarbamoyl]phenoxyacetic acid

Melting point: 268°–270° C. (decomp.) Elemental analysis for $C_{22}H_{17}N_5O_5$ Calcd. (%) C:61.25 H:3.97 N:16.23 Found (%) C:60.88 H:4.33 N:15.97.

Example 50

2-[4-[2-[2-(1H-Tetrazol-5-yl)phenylthio]phenylcarbamoyl]phenoxy]propionic acid

Melting point: 207°–209° C. Elemental analysis for $C_{23}H_{19}N_5O_4S$ Calcd. (%) C:59.86 H:4.15 N:15.18 Found (%) C:59.61 H:4.36 N:15.02.

Example 51

2-Methyl-2-[4-[2-[2-(1H-tetrazol-5-yl)phenylthio]phenylcarbamoyl]phenoxy]propionic acid Melting point: 186°–188° C. (decomp.) Elemental analysis for $C_{24}H_{21}N_5O_4S \cdot \frac{1}{4}H_2O$ Calcd. (%) C:60.05 H:4.51 N:14.59 Found (%) C:60.25 H:4.69 N:14.28.

Example 52

Ethyl 4-[2-[2-(1H-tetrazol-5-yl)phenylthio]phenylcarbamoyl]phenoxyacetate

Melting point: 202°–203° C. Elemental analysis for $C_{24}H_{21}N_5O_4S$ Calcd. (%) C:60.62 H:4.45 N:14.73 Found (%) C:60.57 H:4.53 N:14.71.

Example 53

Propyl 4-[2-[2-(1H-tetrazol-5-yl)phenylthio]phenylcarbamoyl]phenoxyacetate

Melting point: 174°–176° C. Elemental analysis for $C_{25}H_{23}N_5O_4S$ Calcd. (%) C:61.34 H:4.74 N:14.31 Found (%) C:61.56 H:4.84 N:14.31.

Example 54

Isoamyl 4-[2-[2-(1H-tetrazol-5-yl)phenylthio]phenylcarbamoyl]phenoxyacetate

Melting point: 120°–122° C. Elemental analysis for $C_{27}H_{27}N_5O_4S$ Calcd. (%) C:62.65 H:5.26 N:13.53 Found (%) C:62.83 H:5.43 N:13.62.

Example 55

Ethyl 4-[2-[2-(1H-tetrazol-5-yl)phenylsulfinyl]phenylcarbamoyl]pheoxyacetate

Melting point: 215°–216° C. (decomp.) IR $cm^{-1}$(KBr): 3700–2200, 1725, 1605, 1495, 1435, 1250.

Example 56

Ethyl 4-[2-[2-(1H-tetrazol-5-yl)phenylsulfonyl]phenylcarbamoyl]phenoxyacetate

Melting point: 162°–163° C. IR $cm^{-1}$(KBr): 3700–2200, 1740, 1680, 1600, 1500, 1315, 1220.

Example 57

Ethyl 4-[4-[2-[2-(1H-tetrazol-5-yl)phenylsulfinyl]phenylcarbamoyl]phenoxy]butyrate Melting point: 204°–206° C. (decomp.) IR $cm^{-1}$(KBr): 3700–2200, 1730, 1635, 1600, 1300.

Example 58

Ethyl 4-[4-[2-[2-(1H-tetrazol-5-yl)phenylsulfonyl]phenylcarbamoyl]phenoxy]butyrate Melting point: 182°–184° C. IR $cm^{-1}$(KBr): 3700–2200, 3360, 1740, 1670, 1580, 1505, 1325, 1255.

Example 59

Ethyl 6-[4-[2-[2-(1H-tetrazol-5-yl)phenylsufinyl]phenylcarbamoyl]phenoxy]hexanate Melting point: 188°–189° C. IR $cm^{-1}$(KBr): 3700–2200, 1730, 1640, 1605, 1580, 1520, 1500, 1440, 1255.

Example 60

Ethyl 6-[4-[2-[2-(1H-tetrazol-5-yl)phenylsulfonyl]phenylcarbamoyl]phenoxy]hexanate Melting point: 180°–181° C. IR $cm^{-1}$(KBr): 3700–2200, 3360, 1725, 1670, 1605, 1580, 1505, 1320, 1255.

Example 61

Ethyl 4-[4-[2-[2-(1H-tetrazol-5-yl)phenoxy]phenylcarbamoyl]phenoxy]butyrate

Melting point: 162°–164° C. IR $cm^{-1}$(KBr): 3700–2300, 3360, 1730, 1640, 1610, 1510, 1280, 1260.

Example 62

Ethyl 6-[4-[2-[2-(1H-tetrazol-5-yl)phenoxy]phenylcarbamoyl]phenoxy]hexanate

Melting point: 140°–141° C. IR cm$^{-1}$(KBr): 3700–2500, 3350, 2950, 1725, 1640, 1605, 1500, 1260, 1250.

Example 63

Ethyl 2-[4-[2-[2-(1H-tetrazol-5-yl)phenylthio]phenylcarbamoyl]phenoxy]propionate Melting point: 157°–158° C. IR cm$^{-1}$(KBr): 3700–2200, 3380, 1725, 1680, 1600, 1580, 1500, 1435, 1300, 1240.

Example 64

Ethyl 2-methyl-2-[4-[2-[2-(1H-tetrazol-5-yl)phenylthio]phenylcarbamoyl]phenoxy]propionate Melting point: 157°–158° C. IR cm$^{-1}$(KBr): 3700–2200, 3350, 1720, 1640, 1600, 1490, 1470, 1255.

Example 65

Ethyl 4-[2-[4-(1H-tetrazol-5-yl)phenoxy]phenylcarbamoyl]phenoxyacetate

Melting point: 206°–208° C. (decomp.) IR cm$^{-1}$(KBr): 3700–2200, 3420, 1750, 1625, 1605, 1505, 1450, 1220.

Example 66

Ethyl 4-[2-[2-(1H-tetrazol-5-yl)phenoxy]phenylcarbamoyl]phenoxyacetate

Melting point: 162°–163° C. IR cm$^{-1}$(KBr): 3355, 3200–2200, 1745, 1625, 1600, 1495, 1470, 1260, 1220.

Example 67

Butyl 4-[2-[2-(1H-tetrazol-5-yl)phenylthio]phenylcarbamoyl]phenoxyacetate

In a mixture of 6 ml of pyridine and 80 ml of methylene chloride was dissolved 5.3 g of 2-[2-(1H-tetrazol-5-yl)phenylthio]aniline followed by dropwise addition of 5.4 g of butyl 4-chloroformylphenoxyacetate, and the mixture was stirred overnight. The solvent was then distilled off and the residue was crystallized from aqueous ethanol and then recrystallized ethyl acetate to give 8.1 g of the title compound as white crystals, m.p. 133–135.

Elemental analysis for $C_{26}H_{25}N_5O_4S$ Calcd. (%) C:62.01 H:5.00 N:13.91 Found (%) C:61.98 H:5.09 N:13.87.

In the same manner as Example 67, the following compounds were produced.

Example 68

Ethyl 4-[5-chloro-2-[2-(1H-tetrazol-5-yl)phenylthio]phenylcarbamoyl]phenoxyacetate Melting point: 206°–208° C. IR cm$^{-1}$(KBr): 3370, 3100–2300, 1745, 1680, 1600, 1565, 1500, 1410, 1220.

Example 69

Ethyl 4-[5-methoxy-2-[2-(1H-tetrazol-5-yl)phenylthio]phenylcarbamoyl]phenoxyacetate Melting point: 195°–197° C. IR cm$^{-1}$(KBr): 3380, 3200–2300, 1755, 1680, 1600, 1575, 1500, 1450, 1200.

Example 70

Ethyl 4-[3-fluoro-2-[2-(1H-tetrazol-5-yl)phenylthio]phenylcarbamoyl]phenoxyacetate Melting point: 208°–209° C. IR cm$^{-1}$(KBr): 3390, 3200–2300, 1760, 1680, 1600, 1580, 1500, 1465, 1220.

Example 71

Ethyl 2-methoxy-4-[2-[2-(1H-tetrazol-5-yl)phenylthio]phenylcarbamoyl]phenoxyacetate Melting point: 179°–181° C. IR cm$^{-1}$(KBr): 3380, 3100–2300, 1730, 1680, 1580, 1500, 1435, 1270, 1210.

Example 72

Butyl 4-[5-methyl-2-[2-(1H-tetrazol-5-yl)phenylthio]phenylcarbamoyl]phenoxyacetate Melting point: 146°–148° C. IR cm$^{-1}$(KBr): 3380, 3200–2300, 1740, 1685, 1600, 1570, 1500, 1450, 1210.

Example 73

Butyl 4-[2-[2-(1H-tetrazol-5-yl)phenylthio]-5-trifluoromethyl]phenylcarbamoyl]phenoxyacetate Melting point: 190°–192° C. IR cm$^{-1}$(KBr): 3380, 3200–2300, 1760, 1605, 1580, 1530, 1505, 1430, 1335.

Example 74

Butyl 4-[5-fluoro-2-[2-(1H-tetrazol-5-yl)phenylthio]phenylcarbamoyl]phenoxyacetate Melting point: 177°–179° C. IR cm$^{-1}$(KBr): 3360, 3200–2300, 1740, 1680, 1585, 1520, 1500, 1430, 1250.

Example 75

Butyl 4-[4-methyl-2-[2-(1H-tetrazol-5-yl)phenylthio]phenylcarbamoyl]phenoxyacetate Melting point: 161°–162° C. IR cm$^{-1}$(KBr): 3380, 3200–2300, 1740, 1680, 1600, 1500, 1300, 1210.

Example 76

Ethyl 4-[3-chloro-2-[2-(1H-tetrazol-5-yl)phenylthio]phenylcarbamoyl]phenoxyacetate Melting point: 180°–182° C. IR cm$^{-1}$(KBr): 3360, 3200–2300, 1760, 1670, 1605, 1570, 1500, 1450, 1210, 1180.

Example 77

Ethyl 3-[2-[2-(1H-tetrazol-5-yl)phenylthio]phenylcarbamoyl]phenoxyacetate

Melting point: 130°–133° C. IR cm$^{-1}$(KBr): 3370, 3200–2200, 1740, 1675, 1575, 1525.

Example 78

Ethyl 2-[2-[2-(1H-tetrazol-5-yl)phenylthio]phenylcarbamoyl]-phenoxyacetate

Melting point: 145°–146° C. IR cm$^{-1}$(KBr): 3700–2200, 1760, 1635, 1575, 1520.

Example 79

Ethyl 4-[4-[2-(1H-tetrazol-5-yl)phenylthio]phenylcarbamoyl]-phenoxyacetate

Melting point: 232°–234° C. (decomp.) IR cm$^{-1}$(KBr): 3200–2200, 1780, 1650, 1605, 1505.

Example 80

Ethyl 3-[4-[2-(1H-tetrazol-5-yl)phenylthio]phenylcarbamoyl]p-henoxyacetate

Melting point: 176°–179° C. (decomp.) IR cm$^{-1}$(KBr): 3270, 3700–2200, 1740, 1650, 1585, 1525.

Example 81

Ethyl 2-[4-[2-(1H-tetrazol-5-yl)phenylthio]phenylcarbamoyl]-phenoxyacetate

Melting point: 97°–99° C. IR cm$^{-1}$(KBr): 3320, 3700–2200, 1750, 1655, 1585, 1525.

Example 82

Ethyl 4-[2-[3-(1H-tetrazol-5-yl)phenoxy]phenylcarbamoyl]-phenoxyacetate

Melting point: 165°–166° C. IR cm$^{-1}$(KBr): 3700–2200, 1755, 1600, 1500, 1445.

Example 83

Ethyl 4-[2-[4-(1H-tetrazol-5-yl)phenylthio]phenylcarbamoyl]-phenoxyacetate

Melting point: 148°–149° C. IR cm$^{-1}$(KBr): 3380, 3200–2200, 1750, 1670, 1605, 1580, 1520, 1500, 1435, 1300.

Example 84

Ethyl 3-[2-[4-(1H-tetrazol-5-yl)phenylthio]phenylcarbamoyl]-phenoxyacetate

Melting point: 88°–90° C. IR cm$^{-1}$(KBr): 3370, 3200–2200, 1745, 1680, 1650, 1580, 1520, 1490, 1440, 1310, 1200.

Example 85

Ethyl 2-[2-[4-(1H-tetrazol-5-yl)phenylthio]phenylcarbamoyl]-phenoxyacetate

Melting point: 155°–157° C. IR cm$^{-1}$(KBr): 3450, 3200–2200, 1755, 1635, 1600, 1580, 1520, 1490, 1420, 1315, 1205.

In the same manner as Example 6, the following compounds were produced.

Example 86

4-[5-Chloro-2-[2-(1H-tetrazol-5-yl)phenylthio]phenylcarbamoyl]phenoxyacetic acid Melting point: 217°–220° C. Elemental analysis for $C_{22}H_{16}ClN_5O_4S.7/4H_2O$ Calcd. (%) C:51.46 H:3.83 N:13.64 Found (%) C:51.59 H:3.97 N:13.35.

Example 87

4-[5-Methoxy-2-[2-(1H-tetrazol-5-yl)phenylthio]-phenylcarbamoyl]phenoxyacetic acid Melting point: 244°–246° C. Elemental analysis for $C_{23}H_{19}ClN_5O_5S$ Calcd. (%) C:57.85 H:4.01 N:14.67 Found (%) C:57.63 H:4.29 N:14.37.

Example 88

4-[4-[2-(1H-Tetrazol-5-yl)phenylthio]phenylcarbamoyl]phenoxyacetic acid

Melting point: 250°–251° C. (decomp.) Elemental analysis for $C_{22}H_{17}N_5O_4S$ Calcd. (%) C:59.05 H:3.83 N:15.65 Found (%) C:59.02 H:3.63 N:15.45.

Example 89

2-[4-[2-(1H-Tetrazol-5-yl)phenylthio]phenylcarbamoyl]phenoxyacetic acid

Melting point: 257°–259° C. (decomp.) Elemental analysis for $C_{22}H_{17}N_5O_4S.\frac{1}{4}H_2O$ Calcd. (%) C:58.46 H:3.90 N:15.50 Found (%) C:58.43 H:3.98 N:15.49.

Example 90

3-[2-[2-(1H-Tetrazol-5-yl)phenylthio]phenylcarbamoyl]phenoxyacetic acid

Melting point: 214.5°–215.5° C. (decomp.) Elemental analysis for $C_{22}H_{17}N_5O_4S$ Calcd. (%) C:59.05 H:3.83 N:15.65 Found (%) C:59.13 H:3.84 N:15.61.

Example 91

4-[3-Fluoro-2-[2-(1H-tetrazol-5-yl)phenylthio]phenylcarbamoyl]phenoxyacetic acid Melting point: 225°–227° C. Elemental analysis for $C_{22}H_{16}FN_5O_4S.\frac{1}{4}H_2O$ Calcd. (%) C:56.23 H:3.54 N:14.90 Found (%) C:56.08 H:3.84 N:14.98.

Example 92

2-Methoxy-4-[2-[2-(1H-tetrazol-5-yl)phenylthio]-phenylcarbamoyl]phenoxyacetic acid Melting point: 218°–220° C. Elemental analysis for $C_{13}H_{19}N_5O_5S$ Calcd. (%) C:57.85 H:4.01 N:14.67 Found (%) C:57.72 H:4.28 N:14.62.

Example 93

3-[4-[2-(1H-Tetrazol-5-yl)phenylthio]phenylcarbamoyl]phenoxyacetic acid

Melting point: 233-°234° C. (decomp.) Elemental analysis for $C_{22}H_{17}N_5O_4S$ Calcd. (%) C:59.05 H:3.83 N:15.65 Found (%) C:58.85 H:3.60 N:15.60.

Example 94

4-[5-Methyl-2-[2-(1H-tetrazol-5-yl)phenylthio]phenylcarbamoyl]phenoxyacetic acid Melting point: 246°–247° C. Elemental analysis for $C_{23}H_{19}N_5O_4S.1/5H_2O$ Calcd. (%) C:59.40 H:4.20 N:15.06 Found (%) C: 59.40 H: 4.11 N:15.06.

Example 95

4-[2-[3-(1H-Tetrazol-5-yl)phenoxy]phenylcarbamoyl]-phenoxyacetic acid

Melting point: 179°–183° C. Elemental analysis for $C_{22}H_{17}N_5O_5S \cdot \frac{1}{2}H_2O$ Calcd. (%) C:60.62 H:4.06 N:16.07 Found (%) C:60.49 H:4.28 N:15.77.

Example 96

2-[2-[2-(1H-Tetrazol-5-yl)phenylthio]phenylcarbamoyl]phenoxyacetic acid

Melting point: 191°–193° C. (decomp.) Elemental analysis for $C_{22}H_{17}N_5O_4S$ Calcd. (%) C:59.05 H:3.83 N:15.65 Found (%) C:58.84 H:3.84 N:15.46.

Example 97

4-[2-[2-(1H-Tetrazol-5-yl)phenylthio-5-trifluoromethyl]phenylcarbamoyl]phenoxyacetic acid Melting point: 275°–277° C. Elemental analysis for $C_{23}H_{16}F_3N_5O_4S \cdot 7/4H_2O$ Calcd. (%) C:50.50 H:3.59 N:12.80 Found (%) C:50.43 H:3.43 N:12.83.

Example 98

4-[5-Fluoro-2-[2-(1H-tetrazol-5-yl)phenylthio]phenylcarbamoyl]phenoxyacetic acid Melting point: 218°–220° C. Elemental analysis for $C_{22}H_{16}FN_5O_4S \cdot \frac{1}{2}H_2O$ Calcd. (%) C:55.69 H:3.61 N:14.76 Found (%) C:55.83 H:3.87 N:14.71.

Example 99

4-[4-Methyl-2-[2-(1H-tetrazol-5-yl)phenylthio]phenylcarbamoyl]phenoxyacetic acid Melting point: 246°–248° C. Elemental analysis for $C_{23}H_{19}N_5O_4S \cdot \frac{1}{2}H_2O$ Calcd. (%) C:59.28 H:4.22 N:15.03 Found (%) C:59.25 H:4.37 N:14.99.

Example 100

4-[2-[4-(1H-Tetrazol-5-yl)phenylthio]phenylcarbamoyl]phenoxyacetic acid

Melting point: 252°–253° C. (decomp.) Elemental analysis for $C_{22}H_{17}N_5O_4S$ Calcd. (%) C:59.05 H:3.83 N:15.65 Found (%) C:58.99 H:3.88 N:15.55.

Example 101

3-[2-[4-(1H-Tetrazol-5-yl)phenylthio]phenylcarbamoyl]phenoxyacetic acid

Melting point: 285°–288° C. (decomp.) Elemental analysis for $C_{22}H_{17}N_5O_4S \cdot 3/2H_2O$ Calcd. (%) C:55.69 H:4.25 N:14.76 Found (%) C:55.88 H:4.00 N:15.06.

Example 102

2-[2-[4-(1H-Tetrazol-5-yl)phenylthio]phenylcarbamoyl]phenoxyacetic acid

Melting point: 253°–254° C. (decomp.) Elemental analysis for $C_{22}H_{17}N_5O_4S$ Calcd. (%) C:59.05 H:3.83 N:15.65 Found (%) C:58.98 H:3.65 N:15.45.

Example 103

N-[2-[2-(1H-Tetrazol-5-yl)phenylthio]phenyl]-4-[(1H-tetrazol-5-yl)methoxy]benzamide In 10 ml of N,N-dimethylformamide was dissolved 0.77 g of N-[2-(2-cyanophenylthio)phenyl]-4-cyanomethoxybenzamide (prepared by the process described in Reference Example 6) followed by addition of 0.91 g of sodium azide and 0.27 g of ammonium chloride, and the mixture was stirred at 120° for 7 hours. After cooling, the reaction mixture was acidified with diluted hydrochloric acid and the crystals separated out therefrom were collected by filtration and washed with water. The crude crystals thus obtained were recrystallized from ethanol to give 0.7 g of the title compound as white crystals, m.p. 240°–242° C. (decomp.). Elemental analysis for $C_{22}H_{17}N_9O_2S$ Calcd. (%) C:56.04 H:3.63 N:26.74 Found (%) C:56.20 H:3.70 N:26.47.

Example 104

N,N-Dimethylcarbamoylmethyl 4-[2-[2-(1H-tetrazol-5-yl)phenylthio]phenylcarbamoyl]-phenoxyacetate In 15 ml of N,N-dimethylformamide was dissolved 1.2 g of 4-[2-[2-(1H-tetrazol-5-yl)phenylthio]phenylcarbamoyl]p-henoxyacetic acid (prepared in Example 6), followed by addition of 0.44 g of N,N'-carbonyldiimidazole with ice-cooling and stirring. The mixture was stirred with ice-cooling for 20 minutes, then 0.42 g of N,N-dimethylglycolamide was added, and the mixture was stirred at room temperature overnight. This reaction mixture was acidified with acetic acid and diluted with water and the crystals separated out therefrom were collected by filtration and recrystallized from N,N-dimethylformamide-ethyl acetate to give 0.55 g of the title compound as white crystals.

Melting point: 205°–206° C.

Elemental analysis for $C_{26}H_{24}N_6O_5S$. Calcd. (%) C:58.64 H:4.54 N:15.78 Found (%) C:58.36 H:4.70 N:15.66.

In the same manner, the following compound was produced.

Example 105

N,N-Diethylcarbamoylmethyl 4-[2-[2-(1H-tetrazol-5-yl)phenylthio]phenylcarbamoyl]-phenoxyacetate Melting point: 137°–139° C. Elemental analysis for $C_{28}H_{28}N_6O_5S$. Calcd. (%) C:59.99 H:5.03 N:14.99 Found (%) C:59.75 H:5.19 N:14.93.

Example 106

4-[2-[2-(1H-Tetrazol-5-yl)phenylthio]phenylcarbamoyl]phenoxyacetamide

In 6 ml of N,N-dimethylformamide was dissolved 0.63 g of 4-[2-[2-(1H-tetrazol-5-yl)phenylthio]phenylcarbamoyl]phenoxyacetic acid (prepared in Example 6) followed by addition of 0.24 g of N,N'-carbonyldiimidazole. The mixture was stirred at room temperature for 1 hour, and then it was poured in 28% aqueous ammonia and stirred for 1 hour. The reaction mixture was diluted with water and, then, acidified with concentrated hydrochloric acid, and the crystals separated out therefrom were collected by filtration and washed with water. The crude crystals thus obtained were recrystallized from N,N-dimethyl-formamide-ethanol to give 0.52 g of the title compound as white crystals.

Melting point: 229°–231° C. (decomp.) Elemental analysis for $C_{22}H_{18}N_6O_3S$ Calcd. (%) C:59.18 H:4.06 N:18.82 Found (%) C:58.89 H:4.11 N:18.46.

In the same manner, the following compounds were produced.

Example 107

N,N-Diethyl-4-[2-[2-(1H-tetrazol-5-yl)phenyl]phenyl-carbamoyl]phenoxyacetamide

Melting point: 176°–178° C. Elemental analysis for $C_{26}H_{26}N_6O_3S \cdot \frac{1}{2}H_2O$ Calcd. (%) C:61.22 H:5.34 N:16.47 Found (%) C:61.27 H:5.38 N:16.26.

Example 108

N,N-Dimethyl-4-[2-[2-(1H-tetrazol-5-yl)phenylthio]-phenylcarbamoyl]phenoxyacetamide Melting point: 189°–190° C. Elemental analysis for $C_{24}H_{22}N_6O_3S$ Calcd. (%) C:60.75 H:4.67 N:17.71 Found (%) C:60.97 H:4.67 N:17.90.

Example 109

Ethyl 4-[2-[3-chloro-2-(1H-tetrazol-5-yl)phenylthio]phenyl-carbamoyl]phenoxyacetate Melting point: 220°–222° C. (decomp.) Elemental analysis for $C_{24}H_{22}N_6O_3S$ Calcd. (%) C:54.83 H:3.35 N:14.53 Found (%) C:54.97 H:3.52 N:14.45.

Example 110

Butyl 4-[2-[4-chloro-2-(1H-tetrazol-5-yl)phenylthio]phenyl-carbamoyl]phenoxyacetate Melting point: 156°–157° C. IR $cm^{-1}$(KBr): 3370, 3200–2200, 1730, 1675, 1600, 1575, 1525, 1495, 1430.

Example 111

Butyl 4-[2-[3-methoxy-2-(1H-tetrazol-5-yl)phenylthio]phenyl-carbamoyl]phenoxyacetate Melting point: 216°–217° C. Elemental analysis for $C_{27}H_{27}N_5O_5S$ Calcd. (%) C:60.77 H:5.10 N:13.12 Found (%) C:60.51 H:5.15 N:13.06.

Example 112

Butyl 4-[2-[5-methoxy-2-(1H-tetrazol-5-yl)phenylthio]phenyl-carbamoyl]phenoxyacetate Melting point: 169°–171° C. IR $cm^{-1}$(KBr): 3375, 3200–2200, 1755, 1680, 1605, 1580, 1500, 1435, 1300.

Example 113

Butyl 4-[2-[3-methyl-2-(1H-tetrazol-5-yl)phenylthio]phenyl-carbamoyl]phenoxyacetate Melting point: 150°–151° C. Elemental analysis for $C_{27}H_{27}N_5O_5S$ IR $cm^{-1}$(KBr): 3375, 3200–2200, 1750, 1680, 1605, 1580, 1500, 1435, 1300.

Example 114

Ethyl 2-chloro-4-[2-[2-(1H-tetrazol-5-yl)phenylthio]phenyl-carbamoyl]phenoxyacetate Melting point: 208°–209° C. (decomp.) Elemental analysis for $C_{24}H_{20}ClN_5O_4S$ Calcd. (%) C:56.53 H:3.95 N:13.73 Found (%) C:56.34 H:4.03 N:13.72.

Example 115

Butyl 4-[4-methoxy-2-[2-(1H-tetrazol-5-yl)phenylthio]phenyl-carbamoyl]phenoxyacetate Melting point: 152°–154° C. Elemental analysis for $C_{27}H_{27}N_5O_5S$ Calcd. (%) C:60.77 H:5.10 N:13.12 Found (%) C:60.73 H:4.93 N:12.99.

Example 116

Butyl 4-[4-chloro-2-[2-(1H-tetrazol-5-yl)phenylthio]phenyl-carbamoyl]phenoxyacetate Melting point: 168°–170° C. Elemental analysis for $C_{26}H_{24}ClN_5O_4S$ Calcd. (%) C:58.04 H:4.50 N:13.02 Found (%) C:58.06 H:4.49 N:12.99.

Example 117

Butyl 4-[2-[2-(1H-tetrazol-5-yl)phenylthio]phenyl-N-methyl-carbamoyl]phenoxyacetate Melting point: 148°–150° C. IR $cm^{-1}$(KBr): 3200–2300, 1760, 1610, 1560, 1475, 1200, 1170.

Example 118

Ethyl 4-[2-[3-hydroxy-2-(1H-tetrazol-5-yl)phenylthio]phenyl-carbamoyl]phenoxyacetate In 10 ml of toluene was suspended 0.63 g of 3-(2-aminophenylthio)-2-(1H-tetrazol-5-yl)phenol (prepared in Reference Example 12)-followed by addition of a solution of 0.58 g of ethyl 4-chloroformylphenoxyacetate in 2 ml of toluene, and the mixture was refluxed for 2 hours. The solvent was then distilled off and the residue was subjected to silica gel column chromatography using 0.5% methanol-chloroform as the eluent to give 0.66 g of the title compound as white crystals, m.p. 155°–157° C.

IR $cm^{-1}$(KBr): 3430, 3700–2200, 1750, 1650, 1600, 1580, 1500, 1440, 1300.

The following compounds were produced in the same manner as Example 118.

Example 119

Butyl 4-[4-hydroxy-2-[2-(1H-tetrazol-5-yl)phenylthio]phenyl-carbamoyl]phenoxyacetate Melting point: 162°–165° C. Elemental analysis for $C_{26}H_{25}N_5O_5S$ Calcd. (%) C:60.10 H:4.85 N:13.48 Found (%) C:60.03 H:4.80 N:13.24.

Example 120

Butyl 4-[5-hydroxy-2-[2-(1H-tetrazol-5-yl)phenylthio]phenylcarbamoyl]phenoxyacetate Melting point: 207°–209° C. Elemental analysis for $C_{26}H_{25}N_5O_5S \cdot \frac{1}{2}C_2H_5OH$ Calcd. (%) C:59.77 H:5.20 N:12.91 Found (%) C:59.81 H:5.41 N:13.15.

Example 121

Ethyl 4-[2-[5-hydroxy-2-(1H-tetrazol-5-yl)phenylthio]phenyl-carbamoyl]phenoxyacetate Mass spectrum ($C_{24}H_{21}N_5O_5S$) M+:491.

The following compounds were produced in the same manner as Example 6.

Example 122

4-[2-[3-Chloro-2-(1H-tetrazol-5-yl)phenylthio]phenyl-carbamoyl]phenoxyacetic acid Melting point: 245°–247° C. (decomp.) Elemental analysis for $C_{22}H_{16}ClN_5O_4S$ Calcd. (%) C:54.83 H:3.35 N:14.53 Found (%) C:54.97 H:3.52 N:14.45.

Example 123

4-[2-[4-Chloro-2-(1H-tetrazol-5-yl)phenylthio]phenyl-carbamoyl]phenoxyacetic acid Melting point: not lower than 300° C. Elemental analysis for $C_{22}H_{16}ClN_5O_4S \cdot 2H_2O$ Calcd. (%) C:51.02 H:3.89 N:13.52 Found (%) C:51.31 H:3.72 N:13.85.

Example 124

4-[2-[3-Methoxy-2-(1H-tetrazol-5-yl)phenylthio]phenylcarbamoyl]phenoxyacetic acid Melting point: 255°–256° C. (decomp.) Elemental analysis for $C_{23}H_{19}N_5O_5S$ Calcd. (%) C:57.85 H:4.01 N:14.67 Found (%) C:57.80 H:4.08 N:14.47.

Example 125

4-[2-[5-Methoxy-2-(1H-tetrazol-5-yl)phenylthio]-phenylcarbamoyl]phenoxyacetic acid Melting point: 235°–237° C. (decomp.) Elemental analysis for $C_{23}H_{19}N_5O_5S$ Calcd. (%) C:57.85 H:4.01 N:14.67 Found (%) C:57.64 H:4.20 N:14.55.

Example 126

4-[2-[3-Methyl-2-(1H-tetrazol-5-yl)phenylthio]phenyl-carbamoyl]phenoxyacetic acid Melting point: 230°–232° C. (decomp.) Elemental analysis for $C_{23}H_{19}N_5O_4S \cdot \frac{1}{4}H_2O$ Calcd. (%) C:59.28 H:4.22 N:15.03 Found (%) C:59.34 H:4.20 N:14.82.

Example 127

4-[3-Chloro-2-[2-(1H-tetrazol-5-yl)phenylthio]phenyl-carbamoyl]phenoxyacetic acid Melting point: 118°–122° C. Elemental analysis for $C_{22}H_{16}ClN_5O_4S \cdot 5/4H_2O$ Calcd. (%) C:52.38 H:3.70 N:13.88 Found (%) C:52.39 H:3.68 N:13.93.

Example 128

2-Chloro-4-[2-[2-(1H-tetrazol-5-yl)phenylthio]phenylcarbamoyl]phenoxyacetic acid Melting point: 252°–254° C. Elemental analysis for $C_{22}H_{16}ClN_5O_4S$ Calcd. (%) C:54.83 H:3.35 N:14.53 Found (%) C:54.83 H:3.48 N:14.36.

Example 129

4-[4-Chloro-2-[2-(1H-tetrazol-5-yl)phenylthio]phenyl-carbamoyl]phenoxyacetic acid Melting point: 200° C. Elemental analysis for $C_{22}H_{16}ClN_5O_4S \cdot \frac{3}{4}H_2O$ Calcd. (%) C:53.34 H:3.56 N:14.14 Found (%) C:53.34 H:3.48 N:14.10.

Example 130

4-[4-Methoxy-2-[2-(1H-tetrazol-5-yl)phenylthio]-phenylcarbamoyl]phenoxyacetic acid Melting point: 244°–246° C. Elemental analysis for $C_{23}H_{19}N_5O_5S$ Calcd. (%) C:57.85 H:4.01 N:14.67 Found (%) C:57.79 H:4.12 N:14.65.

Example 131

4-[2-[2-(1H-tetrazol-5-yl)phenylthio]phenyl-N-methyl-carbamoyl]phenoxyacetic acid Melting point: 248°–250° C. Elemental analysis for $C_{23}H_{19}N_5O_4S$ Calcd. (%) C:59.86 H:4.15 N:15.18 Found (%) C:59.95 H:4.12 N:15.06.

Example 132

4-[4-Hydroxy-2-[2-(1H-tetrazol-5-yl)phenylthio]phenylcarbamoyl]phenoxyacetic acid Melting point: 228°–230° C. (decomp.) Elemental analysis for $C_{22}H_{17}N_5O_5S \cdot \frac{3}{4}H_2O$ Calcd. (%) C:55.40 H:3.91 N:14.68 Found (%) C:55.65 H:3.84 N:14.57.

Example 133

4-[5-Hydroxy-2-[2-(1H-tetrazol-5-yl)phenylthio]-phenylcarbamoyl]phenoxyacetic acid Melting point: 272°–275° C. (decomp.) Elemental analysis for $C_{22}H_{17}N_5O_5S \cdot \frac{1}{2}H_2O$ Calcd. (%) C:56.28 H:3.76 N:14.92 Found (%) C:56.52 H:3.74 N:14.64.

Example 134

4-[2-[3-Hydroxy-2-(1H-tetrazol-5-yl)phenylthio]-phenylcarbamoyl]phenoxyacetic acid Melting point: 240°–242° C. Elemental analysis for $C_{22}H_{17}N_5O_5S$ Calcd. (%) C:57.01 H:3.70 N:15.11 Found (%) C:56.82 H:3.74 N:14.92.

Example 135

4-[2-[5-Hydroxy-2-(1H-tetrazol-5-yl)phenylthio]-phenylcarbamoyl]phenoxyacetic acid Mass spectrum $(C_{22}H_{17}N_5O_5S)$ M+:463.

The pharmacological test data presented below are intended to illustrate the usefulness of some representative species of the compound of the present invention.

Test Methods

1) Leukotriene D4(LTD4) binding assay

First, 0.2 pmol of $^3H$-LTD4 and 100 μg of the membrane fraction prepared from the guinea pig lung were incubated at 25° C. for 1 hour and then the reaction mixture was filtered through a glass filter. The radioactivity of $^3H$-LTD4 bound to the membrane remaining on the glass filter was determined and this value was regarded as total binding (total).

Similarly, 100 μg of the membrane fraction was incubated with 0.2 pmol of $^3H$-LTD4 in the presence of a large excess of cold LTD4 (0.1 nmol) at 25° C. for 1 hour and the radioactivity of $^3H$-LTD4 bound to the membrane was determined and regarded as nonspecific binding (NSB).

Specific binding (SB) of $^3H$-LTD4 was calculated according to expression (1).

$$SB = total - NSB \qquad (1)$$

To investigate the effect of the test substance on LTD4 receptor binding, the test substance was added at the determination of total binding and the total binding in the presence of the test substance (total') was determined. The percent inhibition was calculated according to expression (2).

$$(total - total')/SB \times 100 \qquad (2)$$

2) Shultz-Dale (SD) reaction

Guinea pigs passively sensitized with anti-bovine serum albumin (BSA) rabbit serum were bled to death and the trachea was isolated. Tracheal chain specimens were prepared according to the method of Takagi et al. [Takagi, K., Takayanagi, I. and Fujie, K.: Chem. Pharm. Bull., 6, 716–720 (1958)].

Each tracheal muscle specimen was suspended in a Magnus bath containing 10 ml of Tyrode solution at 37° C. and after stabilization, contractions induced by $10^{-5}$M histamine were determined.

After washing and stabilization, contractions induced by the antigen in the presence of the test substance and $10^{-5}$M mepyramine were determined. From the percentage of the contraction caused by antigen-antibody reaction relative to the contraction induced by $10^{-5}$M histamine, the percent inhibition relative to the control value was determined.

3) Effect on endogenous leukotriene (LT)-induced experimental asthma

Mepyramine (5 mg/kg), propranolol (0.1 mg/kg) or indomethacin (1 mg/kg) was administered intravenously to guinea pigs passively sensitized with anti-BSA rabbit serum and 5 minutes later the antigen (BSA) was administered intravenously. The resulting airway contractile response was determined by the Konzett-Rossler method [Konzett, H. and Rossler, R.: Naunyn Schmiederbergs Arch. Exp. Pathol. Pharmak.,195, 71–74 (1940)].

The test substance was suspended in 0.5% methylcellulose and administered orally 3 hours before antigen administration. Taking the response on complete obstruction of the airway cannula with a clamp as 100% contraction, the maximal contractile response caused by antigen-antibody reaction was determined and expressed in percentage.

From this value, the percent inhibition by the test substance, relative to the control, was determined.

(4) Effect on experimental asthma

The airway contractile response to intravenous administration of an antigen (benzylpenicilloyl-bovine serum albumin) to guinea pigs passively senstitized with anti-benzylpenicilloyl-bovine gamma globulin guinea pig serum was determined by the Konzett-Rossler method.

The test substance suspended in 0.5% methylcellulose was administered orally and 3 hours later, the airway contractile response caused by antigen-antibody reaction was determined. With the response on complete obstruction of the airway cannula with a clamp taken as 100% contraction, the maximal airway contractile response (expressed in percent) caused by antigen antibody reaction was determined. From this value, the percent inhibition, relative to the control, by the test substance was determined.

The results are presented in the following table. The efficacy of the compound of this invention is quite obvious.

| Example No. | LTD4 binding Assay IC50 (M) | SD reaction IC50 (M) | Endogenous LT-induced experimental asthma p.o. ED50 (mg/kg) | Experimental asthma p.o. ED50 (mg/kg) |
|---|---|---|---|---|
| 7 | 1.8 × 10⁻⁷ | 5.80 × 10⁻⁸ | 0.111 | 3.52 |
| 6 | 28.9%** | 2.72 × 10⁻¹⁰ | 36.2%***** | 37.9%*** |
| 4 | 3.58 × 10⁻⁸ | 20.9%** | 30.9%*** | — |
| 14 | 2.20 × 10⁻⁸ | 60.0%** | 58.3%*** | — |
| 67 | 3.34 × 10⁻⁶ | 7.49 × 10⁻¹¹ | 61.2%**** | 82.6%* |
| 105 | 1.82 × 10⁻⁵ | 3.18 × 10⁻¹⁰ | 29.4%**** | 87.9%* |
| C | 3.82 × 10⁻⁶ | 1.57 × 10⁻⁵ | 0.2 (i.v.) | — |

*denotes inhibition(%) at 10 mg/kg;
**inhibition(%) at $10^{-5}$M
***inhibition(%) at 30 mg/kg;
****inhibition(%) at 0.3 mg/kg
*****inhibition(%) at 0.1 mg/kg.
C represents a control drug (FPL-55712).

In the same manner as Preparation Example 1, tablets each containing 2 mg of the compound of Example 67 of the present invention, 70 mg of lactose, 30 mg of corn starch, 4 mg of hydroxypropylcellulose, 2 mg of magnesium stearate and 2 mg of talc in 110 milligrams was manufactured.

Preparation Example 4

A powder containing 0.1% of the compound of Example 6 of the present invention was manufactured by blending 990 mg of lactose evenly with 10 mg of said compound.

Preparation Example 5

A powder containing 0.1% of the compound of Example 7 of the present invention was manufactured in the same manner as Preparation Example 4.

Preparation Example 6

A powder containing 0.1% of the compound of Example 67 of the present invention was manufactured in the same manner as Preparation Example 4.

We claim:

1. A compound of the formula [I]

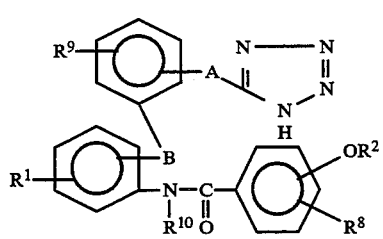

or a pharmacologically acceptable salt thereof wherein
A is —(O)m—(CH(R⁴))n—, wherein R⁴ is hydrogen or alkyl of 1 to 4 carbon atoms, and m and n are each 0 or 1;
B is oxygen or —S(O)p—, wherein p is 0 to 2;
R¹ is hydrogen, alkyl of 1 to 4 carbon atoms, halogen, haloalkyl of 1 to 4 carbon atoms substituted by one to three halogen moieties or hydroxy;
R² is alkyl of 1 to 10 carbon atoms, alkenyl of 2 to 10 carbon atoms, alkyl of 1 to 6 carbon atoms substituted by phenyl, alkyl of 1 or 2 carbon atoms substituted by naphthyl or alkyl of 1 to 10 carbon atoms substituted by COOR³, hydroxy, CON(R⁶)R⁷, quinolin-2-yl, 7-chloroquinolin-2-yl or 1H-tetrazol-5-yl, wherein R³ is hydrogen, alkyl of 1 to 6 carbon atoms or alkyl of 1 to 6 carbon atoms substituted by CON(R⁶)R⁷, and R⁶ and R⁷ are the same or different and each is hydrogen or alkyl of 1 to 4 carbon atoms;

R⁸ is hydrogen, alkoxy of 1 to 4 carbon atoms or halogen;

R⁹ is hydrogen, alkyl of 1 to 4 carbon atoms, alkoxy of 1 to 4 carbon atoms, acyloxy of 2 to 5 carbon atoms, halogen, nitro or hydroxy; and R¹⁰ is hydrogen or alkyl of 1 to 4 carbon atoms.

2. A compound according to claim 1, wherein R² is alkyl of 1 to 10 carbon atoms, alkenyl of 2 to 10 carbon atoms, alkyl of 1 to 6 carbon atoms substituted by phenyl, alkyl of 1 or 2 carbon atoms substituted by naphthyl or alkyl of 1 to 10 carbon atoms substituted by COOR³, hydroxy, CON(R⁶)R⁷, quinolin-2-yl, 7-chloroquinolin-2-yl or 1H-tetrazol-5-yl wherein R³ is hydrogen, alkyl of 1 to 6 carbon atoms or alkyl of 1 to 6 carbon atoms substituted by —CON(R⁶)R⁷ and R⁶ and R⁷ are the same or different and each is hydrogen or alkyl of 1 to 4 carbon atoms.

3. A compound according to claim 2, wherein m and n are zero; B is S(O)$_p$, wherein p is zero; R² is alkyl of 1 to 10 carbon atoms, alkenyl of 2 to 10 carbon atoms, alkyl of 1 to 6 carbon atoms substituted by phenyl, alkyl of 1 or 2 carbon atoms substituted by naphthyl or alkyl of 1 to 10 carbon atoms substituted by —COOR³, hydroxy, CON(R⁶)R⁷, quinolin-2-yl, 7-chloroquinolin-2-yl or 1H-tetrazol-5-yl, wherein R³ is hydrogen, alkyl of 1 to 6 carbon atoms or alkyl of 1 to 6 carbon atoms substituted by —CON(R⁶)R⁷ wherein R⁶ and R⁷ are the same or different and each is hydrogen or alkyl of 1 to 4 carbon atoms.

4. A compound of the formula [I]

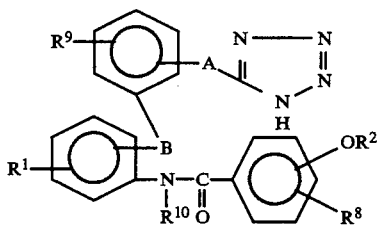

or a pharmaceutically acceptable salt thereof wherein A is —(O)m—(CH(R⁴))n—, wherein R⁴ is hydrogen or alkyl of 1 to 4 carbon atoms;

wherein m and n are zero; B is S(O)$_p$, wherein p is zero; R¹ is hydrogen; R² is alkyl of 1 to 10 carbon atoms, alkenyl of 2 to 10 carbon atoms, alkyl of 1 to 6 carbon atoms substituted by phenyl or alkyl of 1 to 4 carbon atoms substituted by —COOR³ wherein R³ is hydrogen, alkyl of 1 to 6 carbon atoms or alkyl of 1 to 4 carbon atoms substituted by —CON(R⁶)R⁷ wherein R⁶ and R⁷ are the same or different and each is alkyl of 1 to 4 carbon atoms; R⁸ is hydrogen; R⁹ is hydrogen; and R¹⁰ is hydrogen.

5. The compound according to claim 1, which is 4-[2-[2-(1H-tetrazol-5yl)phenylthio]phenylcarbamoyl]phenoxyacetic acid.

6. The compound according to claim 1, which is N-[2-[2-(1H-tetrazol-5-yl)phenylthio]phenyl]-4-(4-phenylbutoxy)benzamide.

7. The compound according to claim 1, which is N-[2-[2-(1H-tetrazol-5-yl)phenylthio]phenyl]-4-hexyloxybenzamide.

8. The compound according to claim 1, which is (E)-N-[2-[2-(1H-tetrazol-5-yl)phenylthio]phenyl]-4-(2-heptenyloxy)benzamide.

9. The compound according to claim 1, which is Butyl 4-[2-[2-(1H-tetrazol-5-yl)phenylthio]phenylcarbamoyl]phenoxyacetate.

10. The compound according to claim 1, which is N,N-diethylcarbamoylmethyl 4-[2-[2-(1H-tetrazol-5-yl)phenylthio]phenylcarbamoyl]phenoxyacetate.

11. A method for treating conditions mediated by SRS-A, in animals and humans, which comprises administering to an animal or human in need thereof a therapeutically effective amount of a compound according to claim 1.

12. A method for treating allergic symptoms in animals and humans, which comprises administering to an animal or human in need thereof a therapeutically effective amount of a compound according to claim 1.

13. A method for treating allergic symptoms in animals and humans, which comprises administering to an animal or human in need thereof a therapeutically effective amount of a compound according to claim 2.

14. A method for treating allergic symptoms in animals and humans, which comprises administering to an animal or human in need thereof a therapeutically effective amount of a compound according to claim 3.

15. A method for treating allergic symptoms in animals and humans, which comprises administering to an animal or human in need thereof a therapeutically effective amount of a compound according to claim 4.

16. A method for treating allergic symptoms in animals and humans, which comprises administering to an animal or human in need thereof a therapeutically effective amount of a compound according to claim 5.

17. A method for treating allergic symptoms in animals and humans, which comprises administering to an animal or human in need thereof a therapeutically effective amount of a compound according to claim 6.

18. A method for treating allergic symptoms in animals and humans, which comprises administering to an animal or human in need thereof a therapeutically effective amount of a compound according to claim 7.

19. A method for treating allergic symptoms in animals and humans, which comprises administering to an animal or human in need thereof a therapeutically effective amount of a compound according to claim 8.

20. A method for treating allergic symptoms in animals and humans, which comprises administering to an animal or human in need thereof a therapeutically effective amount of a compound according to claim 9.

21. A method for treating allergic symptoms in animals and humans, which comprises administering to an animal or human in need thereof a therapeutically effective amount of a compound according to claim 10.

22. A pharmaceutical composition for treating conditions mediated by SRS-A in animals and humans, which comprises a therapeutically effective amount of a compound according to claim 1 in combination with a pharmaceutically acceptable inert dilunent or carrier.

23. A pharmaceutical composition for treating conditions mediated by SRS-A in animals and humans, which comprises a therapeutically effective amount of a compound according to claim 2 in combination with a pharmaceutically acceptable inert dilunent or carrier.

24. A pharmaceutical composition for treating conditions mediated by SRS-A in animals and humans, which comprises a therapeutically effective amount of a compound according to claim 3 in combination with a pharmaceutically acceptable inert dilunent or carrier.

25. A pharmaceutical composition for treating conditions mediated by SRS-A in animals and humans, which comprises a therapeutically effective amount of a compound according to claim 4 in combination with a pharmaceutically acceptable inert dilunent or carrier.

26. A pharmaceutical composition for treating conditions mediated by SRS-A in animals and humans, which comprises a therapeutically effective amount of a compound according to claim 9 in combination with a pharmaceutically acceptable inert dilunent or carrier.

27. A pharmaceutical composition for treating conditions mediated by SRS-A in animals and humans, which comprises a therapeutically effective amount of a compound according to claim 6 in combination with a pharmaceutically acceptable inert dilunent or carrier.

28. A pharmaceutical composition for treating conditions mediated by SRS-A in animals and humans, which comprises a therapeutically effective amount of a compound according to claim 7 in combination with a pharmaceutically acceptable inert dilunent or carrier.

29. A pharmaceutical composition for treating conditions mediated by SRS-A in animals and humans, which comprises a therapeutically effective amount of a compound according to claim 8 in combination with a pharmaceutically acceptable inert dilunent or carrier.

30. A pharmaceutical composition for treating conditions mediated by SRS-A in animals and humans, which comprises a therapeutically effective amount of a compound according to claim 9 in combination with a pharmaceutically acceptable inert dilunent or carrier.

31. A pharmaceutical composition for treating conditions mediated by SRS-A in animals and humans, which comprises a therapeutically effective amount of a compound according to claim 10 in combination with a pharmaceutically acceptable inert dilunent or carrier.

* * * * *

UNITED STATES PATENT AND TRADEMARK OFFICE
CERTIFICATE OF CORRECTION

PATENT NO. : 5,399,703
DATED : March 21, 1995
INVENTOR(S) : Yoshihiko Yoshimoto Et Al It is certified that error appears in the above-identified patent and that said Letters Patent is hereby corrected as shown below:

Claim 26, line 18, "claim 9" should read -- claim 5 --.

Signed and Sealed this

Third Day of October, 1995

Attest:

BRUCE LEHMAN

Attesting Officer     Commissioner of Patents and Trademarks